US012692255B2

(12) United States Patent
Scapozza et al.

(10) Patent No.: US 12,692,255 B2
(45) Date of Patent: Jul. 28, 2026

(54) ADENOSINE 2A RECEPTOR MODULATORS FOR USE IN THE TREATMENT OF CANCER

(71) Applicant: UNIVERSITE DE GENEVE, Geneva (CH)

(72) Inventors: Leonardo Scapozza, Grens (CH); Aurélie Gouiller, Annecy (FR); Margot Boujut, Bons-en-Chablais (FR); Margaux Heritier, Geneva (CH); David Pejoski, Geneva (CH); Thibaut De Smedt, Prévessin-Moëns (FR)

(73) Assignee: UNIVERSITE DE GENEVE, Geneva (CH)

( * ) Notice: Subject to any disclaimer, the term of this patent is extended or adjusted under 35 U.S.C. 154(b) by 0 days.

(21) Appl. No.: 18/862,750

(22) PCT Filed: May 2, 2023

(86) PCT No.: PCT/EP2023/061448

§ 371 (c)(1),
(2) Date: Nov. 4, 2024

(87) PCT Pub. No.: WO2023/213761

PCT Pub. Date: Nov. 9, 2023

(65) Prior Publication Data

US 2025/0115592 A1 Apr. 10, 2025

(30) Foreign Application Priority Data

May 3, 2022 (EP) .................................... 22171440

(51) Int. Cl.
*C07D 413/04* (2006.01)
*A61K 31/4427* (2006.01)
(Continued)

(52) U.S. Cl.
CPC ........ *C07D 413/04* (2013.01); *A61K 31/4439* (2013.01); *A61K 31/4545* (2013.01);
(Continued)

(58) Field of Classification Search
CPC ........ A61P 35/00; A61P 37/04; C07D 401/04; C07D 401/10; C07D 409/10;
(Continued)

(56) References Cited

FOREIGN PATENT DOCUMENTS

DE 10 2005 024245 A1 11/2006
EP 1 302 463 A1 4/2003
(Continued)

OTHER PUBLICATIONS

Betti, Marco et al. "Modifications on the Amino-3,5-Dicyanopyridine Core To Obtain Multifaceted Adenosine Receptor Ligands with Antineuropathic Activity." Journal of medicinal chemistry 62.15 (2019): 6894-6912 (Year: 2019).*
(Continued)

*Primary Examiner* — Savitha M Rao
*Assistant Examiner* — Elena V Vishnyakova
(74) *Attorney, Agent, or Firm* — SALIWANCHIK, LLOYD & EISENSCHENK

(57) ABSTRACT

The present invention relates to new agents useful for in the treatment of cancers, in particular by immunotherapy, as well as pharmaceutically acceptable salts thereof. In particular, this invention provides new A2AR modulators, pharmaceutical compositions and uses thereof.

16 Claims, 1 Drawing Sheet

(51) Int. Cl.

| | |
|---|---|
| ***A61K 31/4436*** | (2006.01) |
| ***A61K 31/4439*** | (2006.01) |
| ***A61K 31/444*** | (2006.01) |
| ***A61K 31/4545*** | (2006.01) |
| ***A61K 31/496*** | (2006.01) |
| ***A61K 31/5377*** | (2006.01) |
| ***A61K 45/06*** | (2006.01) |
| ***A61P 35/00*** | (2006.01) |
| ***A61P 37/04*** | (2006.01) |
| ***C07D 213/85*** | (2006.01) |
| ***C07D 401/04*** | (2006.01) |
| ***C07D 401/10*** | (2006.01) |
| ***C07D 401/14*** | (2006.01) |
| ***C07D 409/10*** | (2006.01) |
| ***C07D 409/14*** | (2006.01) |
| ***C07D 413/14*** | (2006.01) |

(52) U.S. Cl.
CPC ........ *A61K 31/496* (2013.01); *A61K 31/5377* (2013.01); *A61P 35/00* (2018.01); *A61P 37/04* (2018.01); *C07D 213/85* (2013.01); *C07D 401/04* (2013.01); *C07D 401/14* (2013.01); *C07D 409/14* (2013.01); *C07D 413/14* (2013.01)

(58) Field of Classification Search
CPC .. C07D 401/14; C07D 409/14; C07D 413/14; A61K 31/444
See application file for complete search history.

(56) References Cited

FOREIGN PATENT DOCUMENTS

| | | | |
|---|---|---|---|
| EP | 1 304 324 A1 | 4/2003 | |
| WO | WO-0125210 A2 * | 4/2001 | ........... C07D 213/85 |

OTHER PUBLICATIONS

Beavis, Paul A et al. "Adenosine Receptor 2A Blockade Increases the Efficacy of Anti-PD-1 through Enhanced Antitumor T-Cell Responses." Cancer immunology research 3.5 (2015): 506-517 (Year: 2015).*
WO 0125210 A2 English translation (Year: 2001).*
Anderson "The Process of Structure-Based Drug Design". Chemistry & Biology, vol. 10, 787-797, Sep. 2003 (Year: 2003).*
Thiel "Structure-aided drug design's next generation". Nature Biotechnol 2:513-519, 2004 (Year: 2004).*
Sun C et al., (2022) Adenosine-A2A Receptor Pathway in Cancer Immunotherapy. Front. Immunol. 13:837230. (Year: 2022).*
Boujut, M. et al. "Discovery of the First Efficacious Adenosine 2A Receptor Negative Allosteric Modulators for High Adenosine Cancer Immunotherapies" *Journal of Medicinal Chemistry*, Jan. 24, 2025, pp. 4059-4078, vol. 68.
Written Opinion in International Application No. PCT/EP2023/061448, Jul. 20, 2023, pp. 1-9.
Reddy, L. S. et al. "Pd-Mediated Multicomponent Synthesis of Highly Functionalized Pyridines and Consequential C—C Coupling Using Suzuki Reaction in One Pot: Their In Vitro Evaluation as Potential Antibacterial Agents" *Journal of Heterocyclic Chemistry*, Published online Apr. 18, 2014, pp. E104-E113, vol. 51, No. 104.
Gholap, A. R. et al. "Synthesis and evaluation of antifungal properties of a series of the novel 2-amino-5-oxo-4-phenyl-5,6,7,8-tetrahydroquinoline-3-carbonitrile and its analogues" *Bioorganic & Medicinal Chemistry*, 2007, pp. 6705-6715, vol. 15.
Allard, B. et al. "The adenosine pathway in immuno-oncology" *Nature Reviews, Clinical Oncology*, Oct. 2020, pp. 611-629, vol. 17.
Labani-Motlagh, A. et al. "The Tumor Microenvironment: A Milieu Hindering and Obstructing Antitumor Immune Responses" *Frontiers in Immunology*, May 15, 2020, pp. 1-22, vol. 11, Article 940.
Zhong, S. et al. "Targeting Tumor Microenvironment by Small-Molecule Inhibitors" *Translational Oncology*, Jan. 2020, pp. 57-69, vol. 13, No. 1.
Sidders, B. et al. "Adenosine Signaling Is Prognostic for Cancer Outcome and Has Predictive Utility for Immunotherapeutic Response" *Clin Cancer Res*, May 1, 2020, pp. 2176-2187, vol. 26, No. 9.
Vigano, S. et al. "Targeting Adenosine in Cancer Immunotherapy to Enhance T-Cell Function" *Frontiers in Immunology*, Jun. 6, 2019, pp. 1-30, vol. 10, Article 925.
Cekic, C. et al. "Extracellular adenosine regulates naïve T cell development and peripheral maintenance" *The Journal of Experimental Medicine*, 2013, pp. 2693-2706, vol. 210, No. 12.
Lukashev, D. E. et al. "Analysis of A2a receptor-deficient mice reveals No. significant compensatory increases in the expression of A2b, A1, and A3 adenosine receptors in lymphoid organs" *Biochemical Pharmacology*, 2003, pp. 2081-2090, vol. 65.
Zhang, J. et al. "Tumor Immunotherapy Using $A_{2A}$ Adenosine Receptor Antagonists" *Pharmaceuticals*, 2020, pp. 1-14, vol. 13, No. 237.
Franco, R. et al. "Adenosine Receptor Antagonists to Combat Cancer and to Boost Anti-Cancer Chemotherapy and Immunotherapy" *Cells*, Oct. 21, 2021, pp. 1-13, vol. 10, No. 2831.
Seitz, L. et al. "Safety, tolerability, and pharmacology of AB928, a novel dual adenosine receptor antagonist, in a randomized, phase 1 study in healthy volunteers" *Investigational New Drugs,* 2019, pp. 711-721, vol. 37.
Willingham, S. B. et al. "Targeting the A2AR in cancer; early lessons from the clinic" *Current Opinion in Pharmacology*, available online Sep. 29, 2020, pp. 126-133, vol. 53.
Strohl, W. R. et al. "Bispecific T-Cell Redirection versus Chimeric Antigen Receptor (CAR)-T Cells as Approaches to Kill Cancer Cells" *Antibodies*, Jul. 3, 2019, pp. 1-68, vol. 8, No. 41.
Bannas, P. et al. "Nanobodies and Nanobody-Based Human Heavy Chain Antibodies As Antitumor Therapeutics" *Frontiers in Immunology*, Nov. 2017, pp. 1-13, vol. 8, Article 1603.
Willingham, S. B. et al. "A2AR Antagonism with CPI-444 Induces Antitumor Responses and Augments Efficacy to Anti-PD-(L)1 and Anti-CTLA-4 in Preclinical Models" *Cancer Immunology Research*, Oct. 2018, pp. 1136-1149, vol. 6, No. 10.
Murray, T. J. et al. "Synthesis of Heterocyclic Compounds Containing Three Contiguous Hydrogen Bonding Sites in All Possible Arrangements" *Tetrahedron*, 1995, pp. 635-648, vol. 51, No. 2.
Piper, J. R. et al. "Syntheses and Antifolate Activity of 5-Methyl-5-deaza Analogues of Aminopterin, Methotrexate, Folic Acid, and $N^{10}$-Methylfolic Acid" *Journal of Medicinal Chemistry*, 1986, pp. 1080-1087, vol. 29, vol. 6.
Duindam, A. et al. "One Pot Synthesis of 2, 6-Dichloro-3, 5-dicyanopyridine from Aliphatic Precursors" *Synthetic Communications*, 1993 (published online Sep. 24, 2006), cover p. 1-2, pp. 2605-2609, vol. 23, No. 18.
Pan, J. et al. "Cu supported over A1-pillared interlayer clays catalysts for direct hydroxylation of benzene to phenol" *Catalysis Communications*, available online Jun. 9, 2007, pp. 176-181, vol. 9.
Bianchini, G. et al. "Discovery of Novel TRPM8 Blockers Suitable for the Treatment of Somatic and Ocular Painful Conditions: A Journey through $pK_a$ and LogD Modulation" *Journal of Medicinal Chemistry*, Nov. 11, 2021, pp. 16820-16837, vol. 64.
Nicolaou, K. C. et al. "Synthesis and Biological Evaluation of Novel Epothilone B Side Chain Analogues" *ChemMedChem*, Published online Oct. 8, 2015, pp. 1974-1979, vol. 10.
Sarkar, S. et al. "Synthesis of fully-substituted pyridines and dihydropyridines in a highly chemoselective manner utilizing a multicomponent reaction (MCR) strategy" *Royal Society of Chemistry*, Oct. 24, 2014, pp. 53752-53760, vol. 4.
Bruzzese, A. et al. "Insights into adenosine $A_{2A}$ receptor activation through cooperative modulation of agonist and allosteric lipid interactions" *PLOS Computational Biology*, Apr. 16, 2020, pp. 1-39.
Boujut, M. et al. "Discovery of the first-efficacious $A_{2A}$R negative allosteric modulators for high adenosine cancer immunotherapies" *bioRxiv*, Aug. 7, 2024, pp. 1-52.

(56) References Cited

OTHER PUBLICATIONS

Boujut, M. et al. "Optimization of selective and potent $A_2$AR negative allosteric modulators as immunotherapy for high adenosine cancers' treatment" poster, 2023, p. 1.
Imani, S. et al. "Neoantigen mRNA vaccines and $A_2$A receptor antagonism: A strategy to enhance T cell immunity" *Human Vaccines & Immunotherapeutics*, 2025, pp. 1-14, vol. 21, No. 1.
Di Virgilio, F. et al. "Extracellular purines, purinergic receptors and tumor growth" *Oncogene*, published online Jun. 20, 2016, pp. 293-303, vol. 36.
Buisseret, L. et al. "Phase 1 trial of the adenosine A2A receptor antagonist inupadenant (EOS-850): Update on tolerability, and antitumor activity potentially associated with expression of the A2A receptor within the tumor" *ASCO Presentation*, 2021, pp. 1-7.
Ohta, A. "A Metabolic immune Checkpoint: Adenosine in Tumor Microenvironment" *Frontiers in Immunology*, Mar. 29, 2016, pp. 1-11, vol. 7, Article 109.

* cited by examiner

A
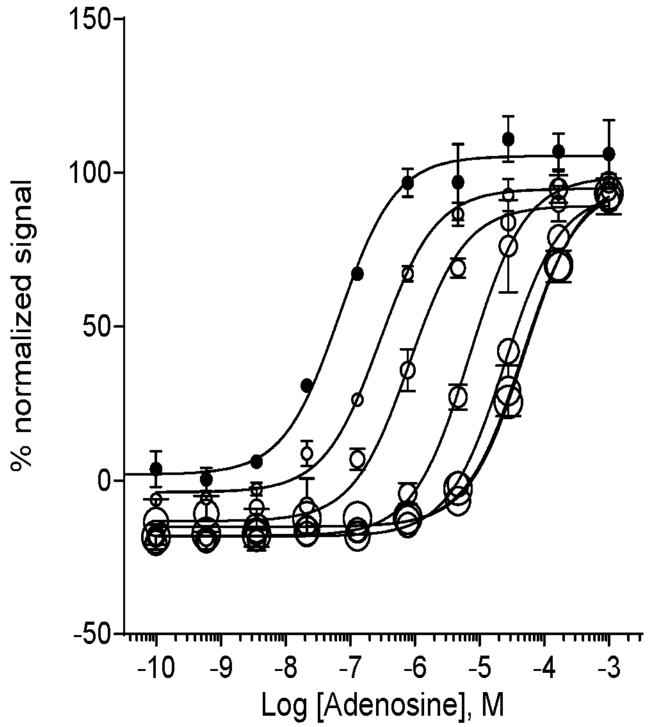
B
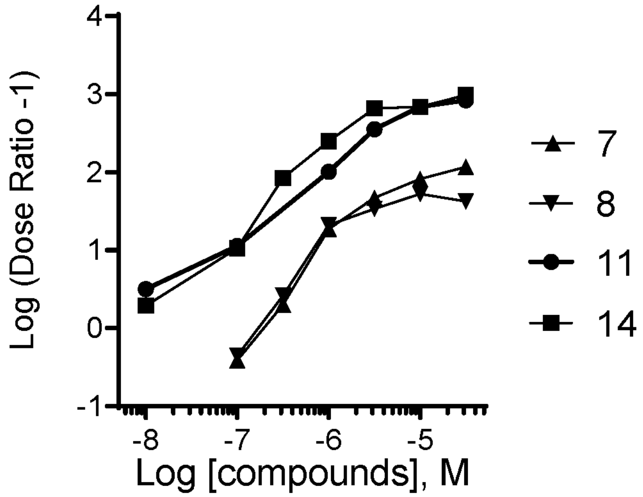

ADENOSINE 2A RECEPTOR MODULATORS FOR USE IN THE TREATMENT OF CANCER

CROSS-REFERENCE TO RELATED APPLICATION

This application is the U.S. national stage application of International Patent Application No. PCT/EP2023/061448, filed May 2, 2023.

FIELD OF THE INVENTION

The present invention relates to adenosine 2A receptor (A2AR) modulators useful for the treatment of cancers, in particular by immunotherapy.

BACKGROUND OF THE INVENTION

High mortality rates and a reduced quality of life are common in patients with many types of solid tumors, demonstrating an urgent need for new anti-tumor treatments. An important component of successful treatment of advanced or relapsing cancers involves reversing the immunosuppression induced by tumors. Current immunotherapies, including immune checkpoint inhibitors (ICI) antibodies, have thus far attempted to restore anti-tumor T cell responses, either by directly targeting these cells or the antigen presenting cells that activate T cells. Despite the clear clinical benefits in approximately 30% of patients, the response rate remains limited. This is partly because of limited penetration of relatively large biomolecule drugs (e.g. antibodies) into solid tumors and drug-mediated effects on only a fraction of anti-tumor immune cell subsets.

To improve the response rate, other therapies aim to address the immunosuppressive tumor microenvironment (TME) (Labani-Motlagh et al., 2020, *Front Immunol.;* 11:940, doi: 10.3389/fimmu.2020.00940). Immunotherapies that can more readily penetrate solid tumors, such as small molecules (Zhong et. Al., 2020, *Trans. Onc., doi.org/* 10.1016/j.tranon.2019.10.001), are also promising candidates for use in combination cancer therapies in order to augment co-administered therapies that are only partially effective on their own.

Adenosine is a naturally-occurring purine nucleoside found in mammals, both intracellularly and extracellularly. Adenosine and its phosphorylated derivatives are involved in many biological processes including energy transfer, cell signaling and vasodilation. Extracellular adenosine (ExAdo), and its receptors, are present in healthy tissues but are also overexpressed in numerous types of solid tumors (Allard et. al., 2020, *Nat. Immunol., Nat Rev Clin Oncol.,* 17(10):611-629, doi: 10.1038 s41571-020-0382-2) and murine models of cancer (Sidders et al., 2020, *Clin Cancer Res.,* 1, 26(9):2176-2187 DOI: 10.1158/1078-0432.CCR-19-2183). Signaling via ExAdo has been demonstrated to cause immunosuppression of immune cells found within the tumor microenvironment (TME) (Vigano et. al., 2019 doi: 10.3389/fimmu.2019.00925). ExAdo mediates this immunosuppression by binding to the extracellular domain of adenosine receptors 2A and 2B (A2AR and A2BR). Therefore, high extracellular adenosine concentrations are a validated cause of immunosuppression in solid tumors because they deactivate tumor-targeting immune cells expressing A2AR. Adenosine has a significantly higher affinity for A2AR, and A2AR plays a more important role in T cell immunity compared to A2BR (Cekic, 2013, *JEM*, doi: 10.10841jem.20130249, Lukashev, 2003, *BioChem Pharmacol.*, doi: 10.1016 S0006-2952(03)00158-8). The remaining two adenosine receptors, A1R and A3R, have different downstream signaling pathways compared to A2AR and A2BR, and their signaling does not normally result in immunosuppression.

A2AR is predominantly found on lymphocyte lineage cells such as T cells and natural killer (NK) cells, as well as on myeloid lineage cells including dendritic cells (DCs), and macrophages (Vigano et al., 2019, supra). Because of the central role of NFκB in many pro-inflammatory and cytotoxic anti-tumor immune responses, the ExAdo signaling pathway could be targeted by therapies to restore desirable immune responses in cancer patients. These responses include the patient's own cellular immunity (T lymphocytes, natural killer cells, dendritic cells, macrophages) as well as the efficacy of co-administered immunotherapies such as immune checkpoint inhibitors (such as anti-PD-1, anti-PD-L1, anti-TIGIT, and anti-CTLA-4 monoclonal antibodies), bispecific antibodies, adoptive cell immunotherapy (e.g. CAR-T cell infusion), and anti-cancer vaccines—all of which would be enhanced within a favorable (proinflammatory) TME.

Blockade of immunosuppressive adenosine signaling, especially A2AR, thus represents a therapeutic strategy with broad applicability in cancer therapy, including as a combination treatment with other approved cancer treatments including radiotherapy, targeted therapies for cancers with specific mutations, and conventional chemotherapy.

Small molecule drugs that block A2AR can be classified as either 'orthosteric' or 'allosteric' antagonists. Orthosteric antagonists bind to the same amino acid motif on A2AR that are engaged by the endogenous receptor ligand, adenosine. On the other hand, allosteric antagonists bind to distinct amino acids motifs that are not utilized by the endogenous ligand.

To effectively block A2AR signaling, orthosteric inhibitors must outcompete adenosine, which is present at high concentrations in many tumors. Achieving this would require high doses of orthosteric A2AR antagonists, which increases the likelihood of undesirable drug-mediated effects.

Orthosteric A2AR antagonists have been developed (Zhang et al., 2020, *Pharmaceuticals,* 13, 237; doi.org/10.3390/ph13090237; Franco et al., 2021, *Cells,* 10, 2831. doi.org/10.3390/cells10112831) but none have thus far entered phase III clinical trials.

Currently, there exists an evident medical need for active agents that are able to act effectively in the immunosuppressive tumor microenvironment for providing novel immunotherapeutic options.

SUMMARY OF THE INVENTION

The present invention is directed to the unexpected finding of cyanopyridine compounds that are able to inhibit signaling of A2AR as A2AR antagonists which are classified as negative allosteric modulators (NAMs) since they achieve an inhibition of the signaling of the target regardless of the extracellular adenosine concentration, including at high micromolar concentrations present within the TME.

It is an object of the invention to provide new therapeutic agents useful for eliciting or increasing an immune response to immunotherapy, in particular anti-cancer immunotherapy.

A first aspect of the invention provides cyanopyridine compounds according to Formula (I), as well pharmaceutically acceptable salts thereof, tautomers, and geometrical isomers.

Another aspect of the invention provides a pharmaceutical composition comprising at least one compound according to the invention, as well pharmaceutically acceptable salts thereof and a pharmaceutically acceptable carrier, diluent or excipient thereof.

A first aspect of the invention provides cyanopyridine compounds according to Formula (I), as well pharmaceutically acceptable salts thereof for use in the treatment of a cancer, in particular solid tumor cancers or malignancies presenting or susceptible of presenting resistance to immunotherapy.

Another aspect of the invention resides in a use of a compound according to the invention for the preparation of a pharmaceutical composition, in particular for the treatment of a cancer, in particular solid tumor cancers or malignancies presenting or susceptible of presenting resistance to immunotherapy.

Another aspect of the invention relates to a pharmaceutical composition comprising at least one compound according to the invention in combination at least one agent useful in the treatment of cancer.

Another aspect of the invention is a method for preventing resistance to anti-cancer immunotherapy and/or treating a cancer in a subject suffering from a cancer or at risk of suffering from resistance to anti-cancer immunotherapy, said method comprising administering a compound according to the invention or a pharmaceutical formulation thereof in a subject in need thereof.

Another aspect of the invention is a method for eliciting or increasing an immune response to immunotherapy, in particular anti-cancer immunotherapy, said method comprising administering an effective amount of one or more compound of the invention or a pharmaceutical formulation thereof in combination with one or more of treatment selected from radiotherapy, chemotherapy, adoptive cell therapy (e.g. Chimeric Antigen Recaptor T cell; CAR-T, or tumor infiltrating lymphocytes; TILs), anti-cancer vaccine therapy, targeted biological therapies (e.g. tumor-specific antibodies) or immunomodulating therapy such as immune checkpoint inhibitors, bispecific T cell engagers, or nanobodies that may bind to a single or multiple drug targets.

Another aspect of the invention is a process for the preparation of a compound according to Formula (I) as defined below.

Further objects and advantageous aspects of the invention will be apparent from the claims and/or from the following detailed description of embodiments of the invention with reference to the annexed drawings.

BRIEF DESCRIPTION OF THE DRAWINGS

FIG. 1 represents the concentration-response curves (CRCs) of adenosine (A) and Schild regression plots (B) obtained with the shift assays of Example 2 with compounds of the invention used to confirm allosteric mode of action. A: the shift assay was performed with compounds and data from compound of the invention (Example 11). The largest open symbols: 30 μM of compound, and a half-log dilution was performed until submicromolar concentrations of the compound-represented by the smallest open circle. Closed circles: the adenosine-only control. B: Schild regression plot calculated for the indicated compounds using the shift assay data.

DETAILED DESCRIPTION OF THE INVENTION

The term "allosteric antagonists" refers to antagonists which block receptor signaling without binding to all or some of the amino acids that the natural ligand (adenosine) uses to bind to the receptor.

The expression "solid tumour cancer" refers to all cancers except cancers of the blood and includes, without being limited to, lung cancer (small cell and non-small cell), breast cancer, ovarian cancer, cervical cancer, uterus cancer, head and neck cancer, melanoma, cancers of the digestive system, hepatocellular carcinoma, colon cancer, rectal cancer, colorectal carcinoma, kidney cancer, prostate cancer, gastric cancer, bronchus cancer, pancreatic cancer, urinary bladder cancer, hepatic cancer and brain cancer.

According to a particular embodiment, a solid tumor cancer with high adenosine signalling, can be characterized by validated RNA transcript signatures in tumor biopsies (Sidders et al., 2020, *Clin Cancer Res.,* 26 (9): 2176-2187, and doi.org/10.1016/j.coph.2020.08.003), pCREB levels in the blood (Seitz, doi.org/10.1007/s10637-018-0706-6), or could possibly be inferred using A2AR expression levels in tumor biopsies (Allard et al., 2020, supra) or in circulating blood immune cells (DOI: 10.3233/JAD-131652).

A solid cancer condition could be considered to feature 'high adenosine signalling' if more than 50% of patients with this type of cancer have more than a five fold increase of adenosine signature genes compared to healthy tissue controls, see Willingham 2020 Curr. Op. Pharm doi.org/10.1016/j.coph.2020.08.003. These cancer conditions include cancers of the digestive system such as of the colon, stomach and pancreas and cancers of the lung, cervix, head and neck.

The expression "immunotherapeutic agent" refers to agents which support the immune system to combat a disease such as cancer. There are currently several major categories: adoptive cellular therapies (e.g. CAR-T cells or other tumor infiltrating immune cells), immune checkpoint inhibitor monoclonal antibodies (ICI mAbs), bispecific T cell engagers (BiTEs), novel immunomodulators or molecular adjuvants, and cancer vaccines, all of which could be envisioned to be used in combination with the present molecules. In addition, standard forms of cancer therapy could be used in combination with the present molecules. These include chemotherapy, radiotherapy, and targeted therapy (specific for particular cancer antigens or cancer-associated molecular pathways). In particular, radiotherapy has been described as an appropriate therapeutic combination to the A2AR-targeting approach (Allard et al., 2020, supra).

The term "bispecific T cell engagers" refers to agents such as antibodies that have one binding arm that recognizes a tumor antigen and another binding arm recognizes an antigen on the surface of a T-cell, as reviewed and exemplified in Strohl et al., 2019, *Antibodies*, doi: 10.3390/antib8030041.

The term "nanobodies refers to agents that are similar to antibodies but typically much lower in molecular weight, reviewed and exemplified in Bannas et. Al., 2017 *Front. Immunology* 10.33891/fmmu.2017.01603.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease.

The term "efficacy" of a treatment according to the invention can be measured based on changes in the course of a disease in response to a use or a method according to the invention. The efficacy of a treatment of a cancer according to the invention can be measured by a reduction of tumour volume, and/or an increase of progression-free survival time and/or increased health and well-being of the subject (e.g. repressing a cancer). Inhibition of cancer cell growth may be evidenced, for example, by arrest of cancer cells in a particular phase of the cell cycle, e.g., arrest at the G2/M phase of the cell cycle. Inhibition of cancer cell growth can also be evidenced using well known imaging methods such as magnetic resonance imaging, computerized axial tomography, PET, SPECT, photo-acoustic imaging, X-rays and fluorescence imaging/detection. Cancer cell growth can also be determined macroscopically via measurements with calipers.

In particular, efficacy of a combined treatment according to the invention can be assessed by reduction of tumour size, disappearance of tumour, or modified expression of biomarkers. These biomarkers may be soluble or expressed by cancer or immune system cells. Biomarkers that can be CAMP and pCREB (Seitz et al., 2019, *Investigational New Drugs,* 37, 711-721; https://doi.org/10.1007/s10637 018 0706 6), or downstream effector molecules that are commonly characterized as anti-tumor immune responses including IL-2, TNF-α or IFN-γ cytokine secretion (Willingham et al., 2018, Cancer Immunol. Res., 6 (10): 1136-1149; DOI: 10.1158/2326-6066.CIR-18-0056).

The term "subject" as used herein, refers to a human or a non-human mammal, such as non-human primate (e.g. chimpanzees and other apes and monkey species), a farm animal (e.g. cattle, sheep, pigs, goats and horses), a domestic mammal (e.g. dogs and cats), or a laboratory animal (e.g. rodents, such as mice, rats and guinea pigs).

The term "efficacy" of a treatment according to the invention can be measured based on changes in the course of disease in response to a use or a method according to the invention. For example, the efficacy of a treatment according to the invention can be measured by its impact on signs or symptoms of illness. A response is achieved when the subject experiences partial or total alleviation, or reduction of unwanted symptoms of illness. According to a particular embodiment, the efficacy can be measured through the assessment of toxin target cleavage or viral replication after infection. For example, the efficacy of a toxin or anti-viral treatment according to the invention can be monitored by following the effect on map kinase kinase 1 cleavage or by the improvement of cell survival, tissue damage and patient survival. The term "aryl" refers to an unsaturated aromatic carbocyclic group of from 6 to 14 carbon atoms having a single ring (e.g., phenyl) or multiple condensed rings (e.g., indenyl, naphthyl). Aryl include phenyl, naphthyl, anthryl, phenanthrenyl and the like.

The term "heteroaryl" refers to a monocyclic or bicyclic unsaturated aromatic moiety of 5 to 10 ring atoms in which one or more of the ring atoms are selected from N, O or S. Particular examples of heteroaryl groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

The term "heteroalkyl" refers to $C_1$-$C_{12}$-alkyl, preferably $C_1$-$C_6$-alkyl, wherein at least one carbon has been replaced by a heteroatom selected from O, N or S, including 2-methoxy ethyl and the like.

The term "heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Heterocycloalkyl include pyrrolidinyl, piperidinyl, piperazinyl, morpholinyl, tetrahydrofuranyl and the like.

The term "alkoxycarbonyl $C_1$-$C_6$ alkyl" refers to $C_1$-$C_6$ alkyl groups having an alkoxycarbonyl substituent, including 2-(benzyloxycarbonyl)ethyl and the like.

Unless otherwise constrained by the definition of the individual substituent, the term "substituted" refers to groups substituted with from 1 to 5 substituents selected from the group consisting of halogen, cyano, nitro, hydroxy, amino (—$NH_2$, —NH—, —N—), amide (—NHC(O)—), carbonyl (—C(O)—), alkoxycarbonyl (—C(O)O—), carboxylic acid, ether (—O—), thioether (—S—), sulfoxide (—S(O)—) and sulfone (—$S(O)_2$—), $C_1$-$C_6$ alkyl, aryl or heteroaryl.

The term "pharmaceutical formulation" refers to preparations which are in such a form as to permit biological activity of the active ingredient(s) to be unequivocally effective and which contain no additional component which would be toxic to subjects to which the said formulation would be administered.

Compounds of the Invention

According to one aspect, is provided a cyanopyridine compound according to Formula (I)

(I)

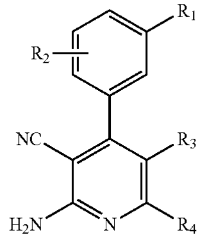

Wherein $R_1$ is selected from aryl optionally substituted by one or more halogen (e.g. fluoro), cyano, hydroxy or $C_1$-$C_6$ alkyl (e.g. optionally substituted phenyl such as phenyl, halogeno phenyl or phenyl optionally substituted by a $C_1$-$C_6$ alkyl such as methyl) and heteroaryl optionally substituted by one or more halogen, cyano, hydroxy or $C_1$-$C_6$ alkyl (e.g. optionally substituted pyridinyl, optionally substituted pyrimidinyl, optionally substituted pyridazinyl, optionally substituted furanyl, optionally substituted indolyl, optionally substituted thiophenyl, optionally substituted pyrazolo, optionally substituted imidazolo, optionally substituted oxazolo, optionally substituted thiazolo, optionally substituted isoxazolo, optionally substituted isothiazolo, optionally substituted triazolo, optionally substituted oxadiazolo, optionally substituted thiodiazolo, optionally substituted tetrazolyl); $R_2$ is selected from H and halogen; $R_3$ is selected from H, CN and optionally substituted $C_1$-$C_6$ alkyl (e.g. $C_1$-$C_6$ alkyl optionally substituted by hydroxy, amino, ether, thioether, cyano, halogen or branched $C_1$-$C_6$ alkyl); $R_4$ is selected from a group XR(R'), an optionally substituted aryl (e.g. optionally substituted phenyl such as phenyl, halogeno phenyl or phenyl optionally substituted by a $C_1$-$C_6$ alkyl such as methyl) and optionally substituted heteroaryl (e.g.

optionally substituted pyridinyl, optionally substituted pyrimidinyl, optionally substituted pyridazinyl, optionally substituted furanyl, optionally substituted indolyl, optionally substituted thiophenyl, optionally substituted pyrazolo, optionally substituted imidazolo, optionally substituted oxazolo, optionally substituted thiazolo, optionally substituted isoxazolo, optionally substituted isothiazolo, optionally substituted triazolo, optionally substituted oxadiazolo, optionally substituted thiodiazolo, optionally substituted tetrazolyl), wherein X is selected from O, S, N and R and R' are independently an optionally substituted $C_1$-$C_6$ alkyl (e.g. a $C_1$-$C_6$ alkyl optionally substituted by hydroxy, amino, ether, thioether, cyano, halogen, aryl, heteroaryl, or a branched $C_1$-$C_6$ alkyl group), or XRR' form together an optionally substituted heterocyclic alkyl (such as optionally substituted azetidine, optionally substituted pyrrolidine, optionally substituted piperidine, optionally substituted morpholinyl, optionally substituted piperazine, optionally substituted azepane, optionally substituted azocane); as well as pharmaceutically acceptable salts thereof for use in treatment of a cancer, in particular in immunotherapy.

According to a further aspect, a cyanopyridine compound according to the invention is a compound of Formula (Ia):

(Ia)

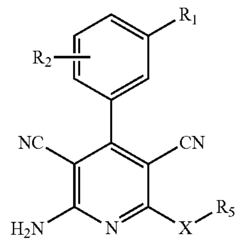

wherein $R_1$ and $R_2$ are as defined herein, X is selected from O and S and $R_5$ is an optionally substituted $C_1$-$C_6$ alkyl (e.g. a $C_1$-$C_6$ alkyl optionally substituted by hydroxy, amino, ether, thioether, cyano, halogen, aryl, heteroaryl, or a branched $C_1$-$C_6$ alkyl group); as well as pharmaceutically acceptable salts thereof.

According to a further aspect, a cyanopyridine compound according to the invention is a compound of Formula (Ib):

(Ib)

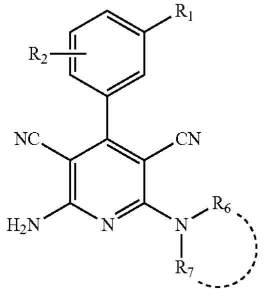

wherein $R_1$ and $R_2$ are as defined herein and $R_6$ and $R_7$ are independently an optionally substituted $C_1$-$C_6$ alkyl (e.g. a $C_1$-$C_6$ alkyl optionally substituted by hydroxy, amino, ether, thioether, cyano, halogen, aryl, heteroaryl, or a branched $C_1$-$C_6$ alkyl group) or form together an optionally substituted heterocyclic alkyl (e.g. optionally substituted azetidine, optionally substituted pyrrolidine, optionally substituted piperidine, optionally substituted morpholinyl, optionally substituted piperazine, optionally substituted azepane, optionally substituted azocane); as well as pharmaceutically acceptable salts thereof.

According to a further aspect, a cyanopyridine compound according to the invention is a compound of Formula (I) wherein $R_3$ is selected from H and optionally substituted $C_1$-$C_6$ alkyl and $R_4$ is selected from an optionally substituted aryl (e.g. optionally substituted phenyl such as phenyl, halogeno phenyl or phenyl optionally substituted by a $C_1$-$C_6$ alkyl such as methyl) and an optionally substituted heteroaryl (e.g. optionally substituted pyridinyl, optionally substituted pyrimidinyl, optionally substituted pyridazinyl, optionally substituted furanyl, optionally substituted indolyl, optionally substituted thiophenyl, optionally substituted pyrazolo, optionally substituted imidazolo, optionally substituted oxazolo, optionally substituted thiazolo, optionally substituted isoxazolo, optionally substituted isothiazolo, optionally substituted triazolo, optionally substituted oxadiazolo, optionally substituted thiodiazolo, optionally substituted tetrazolyl).

According to another aspect, is provided a cyanopyridine compound according to Formula (I)

(I)

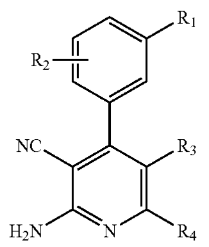

wherein $R_1$ to $R_4$ are as defined herein with the proviso that the compound of Formula (I) is not one of the following compounds:

4-(3-(1H-pyrrol-1-yl)phenyl)-2-amino-6-(benzylthio)pyridine-3,5-dicarbonitrile (RN: 391667-62-2); 2-amino-6-(benzylthio)-4-(3-(2,5-dimethyl-1H-pyrrol-1-yl)phenyl)pyridine-3,5-dicarbonitrile (RN: 391664-25-8); 4-(3-(1H-pyrrol-1-yl)phenyl)-2-amino-6-methoxypyridine-3,5-dicarbonitrile (RN: 391664-24-7); 4-(3-(1H-imidazol-1-yl)phenyl)-2-amino-6-methoxypyridine-3,5-dicarbonitrile; 4-(3-(1H-imidazol-2-yl)phenyl)-2-amino-6-methoxypyridine-3,5-dicarbonitrile; 2-amino-4-(3'-cyano-5'-fluoro-[1,1'-biphenyl]-3-yl)-6-phenylpyridine-3,5-dicarbonitrile (RN: 1646173-41-2); 2-amino-4-(3'-(hydroxymethyl)-[1,1'-biphenyl]-3-yl)-6-phenylpyridine-3,5-dicarbonitrile (RN: 1646173-42-3); 2-amino-4-(4'-chloro-[1,1'-biphenyl]-3-yl)-6-phenylpyridine-3,5-dicarbonitrile (RN: 1646173-50-3); 2-amino-4-(3'-chloro-[1,1'-biphenyl]-3-yl)-6-phenylpyridine-3,5-dicarbonitrile (RN: 1646173-49-0); 2-amino-4-(2'-chloro-[1,1'-biphenyl]-3-yl)-6-phenylpyridine-3,5-dicarbonitrile (RN: 1646173-48-9); 2-amino-6-phenyl-4-(4'-(trifluoromethyl)-[1,1'-biphenyl]-3-yl)pyridine-3,5-dicarbonitrile (RN: 1646173-44-5); 2-amino-6-phenyl-4-(3'-(trifluoromethyl)-[1,1'-biphenyl]-3-yl)pyridine-3,5-dicarbonitrile (RN: 1646173-46-7); 2-amino-4-(3',4'-dichloro-[1,1'-biphenyl]-3-yl)-6-phenylpyridine-3,5-dicarbonitrile (RN: 1646173-51-4); 2-amino-4-(4'-bromo-[1,1'-biphenyl]-3-yl)-6-phenylpyridine-3,5- dicarbonitrile (RN: 1646173-55-8); or 2-amino-4-(2'-methyl-[1,1'-biphenyl]-3-yl)-6-phenylpyridine-3,5-dicarbonitrile (RN: 1646173-54-7).

According to another aspect, is provided a cyanopyridine compound according to Formula (I)

(I)

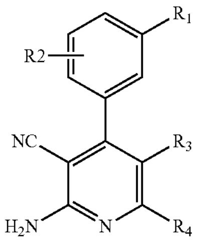

for use as a medicament wherein $R_1$ to $R_4$ are as defined herein with the proviso as defined above.

In a particular embodiment, $R_1$ is an aryl optionally substituted by one or more halogen (e.g. fluoro), cyano, hydroxy or $C_1$-$C_6$ alkyl (e.g. methyl).

In a further particular embodiment, $R_1$ is a phenyl optionally substituted by one or more halogen (e.g. fluoro), cyano, hydroxy or $C_1$-$C_6$ alkyl (e.g. methyl).

In a further particular embodiment, $R_1$ is a phenyl optionally substituted by one or more halogen or $C_1$-$C_6$ alkyl, such as phenyl, halogeno phenyl such as 2-fluorophenyl, 3-fluorophenyl, 4-fluorophenyl or a $C_1$-$C_6$ alkyl phenyl such as methylphenyl like 2-methylphenyl, 3-methylphenyl, 4-methylphenyl.

In another particular embodiment $R_1$ is an heteroaryl optionally substituted by one or more halogen, cyano, hydroxy or $C_1$-$C_6$ alkyl.

In a further particular embodiment, $R_1$ is selected from optionally substituted pyridinyl (e.g. pyridin-2-yl, pyridin-3-yl, pyridin-4-yl), optionally substituted thiophenyl (e.g. thiophen-2-yl, thiophen-3-yl), optionally substituted pyrazolyl (e.g. pyrazol-5-yl) and optionally substituted tetrazolyl, wherein optionally substituted refers to an optional substitution by one or more halogen, cyano, hydroxy or $C_1$-$C_6$ alkyl.

In a further particular embodiment, $R_1$ is an optionally substituted pyridinyl wherein optionally substituted refers to an optional substitution by one or more halogen, cyano, hydroxy or $C_1$-$C_6$ alkyl such as pyridin-2-yl, pyridin-3-yl, pyridin-4-yl, 3-fluoro-2-pyridinyl, 2-fluoro-3-pyridinyl, 6-fluoro-2-pyridinyl, 4-fluoro-2-pyridinyl and 5-fluoro-3pyridinyl.

In a further particular embodiment, $R_1$ is an optionally substituted oxazolyl such as 1,3,4-oxadiazolyl.

In another particular embodiment $R_1$ is a non-substituted heteroaryl.

In a particular embodiment, $R_2$ is H.

In a particular embodiment, $R_3$ is CN.

In a particular embodiment, R is a group XR(R') as defined herein.

In a particular embodiment, $R_4$ is a group OR wherein R is an optionally substituted alkyl such as methyl, ethyl hydroxy ethyl.

In a particular embodiment, $R_4$ is a group SR wherein R is an optionally substituted alkyl such as optionally substituted ethyl phenyl.

In a further particular embodiment, $R_4$ is a group XR(R') wherein XRR' form together an optionally substituted heterocyclic alkyl (such as optionally substituted azetidine, optionally substituted pyrrolidine, optionally substituted piperidine, optionally substituted morpholinyl, optionally substituted piperazine, optionally substituted azepane, optionally substituted azocane).

In a further particular embodiment, $R_4$ is selected from pyridine, pyrrolidine and azetidine.

In a further particular embodiment, $R_4$ is optionally substituted pyridine.

In a further particular embodiment, $R_4$ is piperidine.

In a further particular embodiment, X is N.

In a further particular embodiment, X is O.

In a further particular embodiment, X is S.

According to a further aspect, the cyanopyridine compound is a compound of Formula (Ib), wherein $R_6$ and $R_7$ form together an optionally substituted heterocyclic alkyl.

According to a further aspect, the cyanopyridine compound is a compound of Formula (Ib), wherein $R_6$ and $R_7$ form together an optionally substituted azetidine or an optionally substituted piperidine.

According to a particular embodiment are provided negative allosteric modulators (NAMs) of A2AR.

Compounds of the present invention include in particular those selected from the following group:

4-([1,1'-biphenyl]-3-yl)-2-amino-6-(azetidin-1-yl)pyridine-3,5-dicarbonitrile;

4-([1,1'-biphenyl]-3-yl)-2-amino-6-(pyrrolidin-1-yl)pyridine-3,5-dicarbonitrile;

4-([1,1'-biphenyl]-3-yl)-2-amino-6-(piperidin-1-yl)pyridine-3,5-dicarbonitrile;

2-amino-4-(2'-fluoro-[1,1'-biphenyl]-3-yl)-6-(piperidin-1-yl)pyridine-3,5-dicarbonitrile;

2-amino-4-(3'-fluoro-[1,1'-biphenyl]-3-yl)-6-(piperidin-1-yl)pyridine-3,5-dicarbonitrile;

2-amino-4-(3'-fluoro-[1,1'-biphenyl]-3-yl)-6-(piperidin-1-yl)pyridine-3,5-dicarbonitrile 2-amino-4-(2'-methyl-[1,1'-biphenyl]-3-yl)-6-(piperidin-1-yl)pyridine-3,5-dicarbonitrile;

2-amino-4-(3'-methyl-[1,1'-biphenyl]-3-yl)-6-(piperidin-1-yl)pyridine-3,5-dicarbonitrile 2-amino-4-(4'-methyl-[1,1'-biphenyl]-3-yl)-6-(piperidin-1-yl)pyridine-3,5-dicarbonitrile;

2-amino-6-(piperidin-1-yl)-4-(3-(pyridin-2-yl)phenyl)pyridine-3,5-dicarbonitrile;

2-amino-6-(piperidin-1-yl)-4-(3-(pyridin-3-yl)phenyl)pyridine-3,5-dicarbonitrile;

2-amino-6-(piperidin-1-yl)-4-(3-(pyridin-4-yl)phenyl)pyridine-3,5-dicarbonitrile;

2-amino-6-(piperidin-1-yl)-4-(3-(thiophen-2-yl)phenyl)pyridine-3,5-dicarbonitrile;

2-amino-6-(piperidin-1-yl)-4-(3-(thiophen-3-yl)phenyl)pyridine-3,5-dicarbonitrile;

4-(3-(1H-pyrazol-5-yl)phenyl)-2-amino-6-(piperidin-1-yl)pyridine-3,5-dicarbonitrile;

4-(3-(1H-tetrazol-5-yl)phenyl)-2-amino-6-(piperidin-1-yl)pyridine-3,5-dicarbonitrile;

4-([1,1'-biphenyl]-3-yl)-2-amino-6-(diethylamino)pyridine-3,5-dicarbonitrile;

4-([1,1'-biphenyl]-3-yl)-2-amino-6-morpholinopyridine-3,5-dicarbonitrile;

4-([1,1'-biphenyl]-3-yl)-2-amino-6-(bis(2-hydroxyethyl)amino)pyridine-3,5-dicarbonitrile;

4-([1,1'-biphenyl]-3-yl)-2-amino-6-(4-methylpiperazin-1-yl)pyridine-3,5-dicarbonitrile;

4-([1,1'-biphenyl]-3-yl)-2-amino-6-((2-hydroxyethyl)amino)pyridine-3,5-dicarbonitrile;

4-([1,1'-biphenyl]-3-yl)-2-amino-6-(diisopropylamino)pyridine-3,5-dicarbonitrile;
4-([1,1'-biphenyl]-3-yl)-2-amino-6-(benzylamino)pyridine-3,5-dicarbonitrile;
4-([1,1'-biphenyl]-3-yl)-2-amino-6-(benzylthio)pyridine-3,5-dicarbonitrile;
4-([1,1'-biphenyl]-3-yl)-2-amino-6-methoxypyridine-3,5-dicarbonitrile;
4-([1,1'-biphenyl]-3-yl)-2-amino-6-ethoxypyridine-3,5-dicarbonitrile;
4-([1,1'-biphenyl]-3-yl)-2-amino-6-(2-hydroxyethoxy)pyridine-3,5-dicarbonitrile;
4-([1,1'-biphenyl]-3-yl)-2-amino-6-(benzyloxy)pyridine-3,5-dicarbonitrile;
2-amino-4-(3-(3-fluoropyridin-2-yl)phenyl)-6-(piperidin-1-yl)pyridine-3,5-dicarbonitrile;
2-amino-4-(3-(6-fluoropyridin-2-yl)phenyl)-6-(piperidin-1-yl)pyridine-3,5-dicarbonitrile;
2-amino-4-(3-(4-fluoropyridin-2-yl)phenyl)-6-(piperidin-1-yl)pyridine-3,5-dicarbonitrile;
2-amino-4-(3-(5-fluoropyridin-3-yl)phenyl)-6-(piperidin-1-yl)pyridine-3,5-dicarbonitrile;
2-amino-4-(3-(2-fluoropyridin-3-yl)phenyl)-6-(piperidin-1-yl)pyridine-3,5-dicarbonitrile;
2-amino-4-(2-fluoro-5-(pyridin-3-yl)phenyl)-6-(piperidin-1-yl)pyridine-3,5-dicarbonitrile;
2-amino-4-(2-fluoro-3-(pyridin-3-yl)phenyl)-6-(piperidin-1-yl)pyridine-3,5-dicarbonitrile;
2-amino-4-(3-fluoro-5-(pyridin-3-yl)phenyl)-6-(piperidin-1-yl)pyridine-3,5-dicarbonitrile and
4-(3-(1,3,4-oxadiazol-2-yl)phenyl)-2-amino-6-(piperidin-1-yl)pyridine-3,5-dicarbonitrile.

According to a particular embodiment, the compounds of the invention are selected from the following group:

4-([1,1'-biphenyl]-3-yl)-2-amino-6-(azetidin-1-yl)pyridine-3,5-dicarbonitrile;
4-([1,1'-biphenyl]-3-yl)-2-amino-6-(pyrrolidin-1-yl)pyridine-3,5-dicarbonitrile;
4-([1,1'-biphenyl]-3-yl)-2-amino-6-(piperidin-1-yl)pyridine-3,5-dicarbonitrile;
2-amino-4-(2'-fluoro-[1,1'-biphenyl]-3-yl)-6-(piperidin-1-yl)pyridine-3,5-dicarbonitrile;
2-amino-4-(3'-fluoro-[1,1'-biphenyl]-3-yl)-6-(piperidin-1-yl)pyridine-3,5-dicarbonitrile;
2-amino-4-(3'-fluoro-[1,1'-biphenyl]-3-yl)-6-(piperidin-1-yl)pyridine-3,5-dicarbonitrile
2-amino-4-(2'-methyl-[1,1'-biphenyl]-3-yl)-6-(piperidin-1-yl)pyridine-3,5-dicarbonitrile;
2-amino-4-(3'-methyl-[1,1'-biphenyl]-3-yl)-6-(piperidin-1-yl)pyridine-3,5-dicarbonitrile
2-amino-4-(4'-methyl-[1,1'-biphenyl]-3-yl)-6-(piperidin-1-yl)pyridine-3,5-dicarbonitrile;
2-amino-6-(piperidin-1-yl)-4-(3-(pyridin-2-yl)phenyl)pyridine-3,5-dicarbonitrile;
2-amino-6-(piperidin-1-yl)-4-(3-(pyridin-3-yl)phenyl)pyridine-3,5-dicarbonitrile;
2-amino-6-(piperidin-1-yl)-4-(3-(pyridin-4-yl)phenyl)pyridine-3,5-dicarbonitrile;
2-amino-6-(piperidin-1-yl)-4-(3-(thiophen-2-yl)phenyl)pyridine-3,5-dicarbonitrile;
2-amino-6-(piperidin-1-yl)-4-(3-(thiophen-3-yl)phenyl)pyridine-3,5-dicarbonitrile;
4-(3-(1H-pyrazol-5-yl)phenyl)-2-amino-6-(piperidin-1-yl)pyridine-3,5-dicarbonitrile; and
4-(3-(1H-tetrazol-5-yl)phenyl)-2-amino-6-(piperidin-1-yl)pyridine-3,5-dicarbonitrile.

The compounds of invention have been named according to the IUPAC standards used in the program Chemdraw Professional® (product version 16.0).

Compositions

Pharmaceutical compositions of the invention can contain one or more compounds according to the invention and a pharmaceutically acceptable carrier, diluent or excipient thereof.

According to another particular aspect, the A2AR modulation effects can be achieved through the delivery of formulations compounds of the invention by various routes, preferably orally. According to a particular aspect, compositions further comprise a compound useful in a prevention and/or treatment of a cancer, in particular in cancer immunotherapy.

Compositions of this invention may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

According to a particular embodiment, compositions according to the invention are for oral delivery.

In another particular aspect, compositions according to the invention are adapted for delivery by single or multiple administrations.

According to a particular embodiment, compositions of the invention are veterinary compositions.

Further materials as well as formulation processing techniques and the like are set out in *Remington: The Science & Practice of Pharmacy,* $23^{rd}$ Edition, 2020, Ed. Adeboye Adejare, Academic Press, which is incorporated herein by reference.

According to a particular aspect, is provided a pharmaceutical composition comprising at least one compound according to the invention and a pharmaceutically acceptable carrier, diluent or excipient thereof.

The invention provides compounds of the invention, compositions thereof and methods using the same useful in the prevention and/or treatment of a medical disorder, in particular as A2AR modulators for preventing and/or treating cancers, in particular for use in immunotherapy.

Mode of Administration

Compounds and compositions of this invention may be administered or delivered in any manner including, but not limited to, orally, parenterally, sublingually, transdermally, transmucosally, topically, via inhalation, intra or peri-tumorally, via buccal or intranasal administration, or combinations thereof. Parenteral administration includes, but is not limited to, intra-venous, intra-arterial, intra-peritoneal, subcutaneous and intra-muscular.

In another particular embodiment, a compound according to the invention is administered orally.

In another particular embodiment, a compound according to the invention is administered rectally.

In another particular embodiment, a compound according to the invention is administered intravenously.

The dosage administered, as single or multiple doses, to an individual will vary depending upon a variety of factors, including pharmacokinetic properties, subject conditions and characteristics (sex, age, body weight, health, and size), extent of symptoms, concurrent treatments, frequency of treatment and the effect desired.

Combination

According to one embodiment of the invention, the compounds according to the invention and pharmaceutical formulations thereof can be administered alone or in combination with a co-agent useful in the prevention and/or treatment of a disease.

According to one aspect, compounds of the invention can be administered in combination with at least one therapeutic molecule useful in the treatment of a cancer, in particular in cancer immunotherapy.

According to one aspect, compounds of the invention are to be administered in combination with one or more of treatment selected from radiotherapy, chemotherapy, adoptive cell therapy (e.g. Chimeric Antigen Recaptor T cell; CAR-T, or tumor infiltrating lymphocytes; TILs), anti-cancer vaccine therapy, targeted biological therapies (e.g. tumor-specific antibodies) or immunomodulating therapy such as immune checkpoint inhibitors, bispecific T cell engagers, or nanobodies that may bind to a single or multiple drug targets.

According to one aspect, compounds of the invention can be administered in combination with an anticancer vaccine or at least one immune check point inhibitor such as at least one PD-1, PD-L1 or CTLA4 inhibitor or a combination thereof.

According to a further aspect, at least one immune check point inhibitor is selected from a PD-1 inhibitor and a CTLA4 inhibitor.

According to a further aspect, compounds of the invention are to be administered in combination with an anticancer vaccine wherein the said anticancer vaccine elicits cancer-specific immunity and the compounds of the invention are to be administered before and/or after the anti-cancer vaccine administration.

According to a further aspect, compounds of the invention are to be administered in combination with a cellular therapy, such as in combination with Chimeric Antigen Receptor (CAR) T cells (CAR T cell therapy) or tumor infiltrating lymphocytes (TILs) (bulk TIL cell-based cell therapy) that have been expanded ex vivo. Chimeric Antigen Receptor (CAR) T cells are expanded ex vivo according to a standard method, said method comprising:

- providing at least one genetically modified T cell in a T cell culture medium wherein said genetically modified T cell expresses on its membrane surface a polypeptide specific for a tumor-associated antigen;
- expanding and harvesting the genetically modified T cell in said culture medium.

TTLs are expanded ex vivo according to a standard method, said method comprising:

- isolation of a polyclonal mixture of T cells from tumor fragments;
- expanding these polyclonal T cells in culture medium.

According to a further aspect, compounds of the invention are to be administered in combination with said expanded Chimeric Antigen Receptor (CAR) T cells or TTLs by the same or different routes.

The invention encompasses the administration of a compound of the invention wherein the compound is administered to a subject prior to, simultaneously or sequentially with a therapeutic regimen or at least one co-agent. The compound according to the invention that is administered simultaneously with said at least one co-agent can be administered in the same or different compositions and in the same or different routes of administration.

Subjects

In an embodiment, subjects according to the invention are suffering from a cancer.

In a further particular embodiment, subjects according to the invention are subjects suffering from a solid tumor cancer selected from, but not limited to, lung cancer (small cell and non-small cell), breast cancer, ovarian cancer, cervical cancer, uterus cancer, head and neck cancer, melanoma, cancers of the digestive system, hepatocellular carcinoma, colon cancer, rectal cancer, colorectal carcinoma, kidney cancer, prostate cancer, gastric cancer, bronchus cancer, pancreatic cancer, urinary bladder cancer and hepatic cancer.

In an embodiment, subjects according to the invention are subjects presenting tumors with elevated: adenosine signaling gene signatures, expression of pCREB, or A2AR as described above.

In a further particular embodiment, subjects according to the invention are subjects suffering from a solid tumor cancer are cancers from the digestive system, in particular pancreatic and colorectal cancer.

Use According to the Invention

In a particular embodiment, the invention provides compounds, methods, uses and compositions useful in the treatment of a cancer, in particular in immunotherapy.

According to a further particular embodiment, methods, uses and compositions of the invention are useful for decreasing the development of tumors and/or to potentiate other cancer treatments including radiotherapy, chemotherapy, adoptive cell therapy (e.g. CAR-T), anti-cancer vaccine therapy, targeted biological therapies (e.g. tumor-specific antibodies) or immunomodulating therapy such as immune checkpoint inhibitors.

Another aspect of the invention is a method for preventing resistance to anti-cancer immunotherapy and/or treating a cancer in a subject suffering from a cancer or at risk of suffering from resistance to anti-cancer immunotherapy, said method comprising administering a compound according to the invention or a pharmaceutical formulation thereof in a subject in need thereof.

Another aspect of the invention is a method for eliciting or increasing an immune response to immunotherapy, in particular anti-cancer immunotherapy, said method comprising administering an effective amount of one or more compound of the invention or a pharmaceutical formulation thereof in combination with an immunotherapeutic agent or in combination with radiotherapy in a subject in need thereof.

In a particular embodiment, the invention provides compounds, methods, uses and compositions which are useful for the treatment of a solid tumor cancer in the form of a combination wherein at least one compound of the invention is to be administered in combination with at least one anti-cancer immunotherapeutic agent.

According to a particular aspect, is provided a method for treating a subject suffering from a cancer, said method comprising administering an effective amount of one or more compound of the invention in combination with at least anti-cancer treatment, in particular an anti-cancer immunotherapeutic agent in a subject in need thereof.

According to another particular embodiment, compounds, methods and compositions of the invention are useful in combination with a cellular therapy, in particular for improving a immunosuppressive tumor microenvironment, thereby enhancing infiltration of infused cellular therapies into the tumor. According to a further aspect, the combination increases the ability of T cells to kill cancer cells at the disease site.

References cited herein are hereby incorporated by reference in their entirety. Such modifications are intended to fall within the scope of the appended claims. The invention having been described, the following examples are presented by way of illustration, and not limitation.

Synthesis of Compounds of the Invention

The compounds according to Formula (I) can be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

The general synthetic approaches for obtaining compounds of Formula (I) are depicted in Schemes 1 to 5 below.

Scheme 1

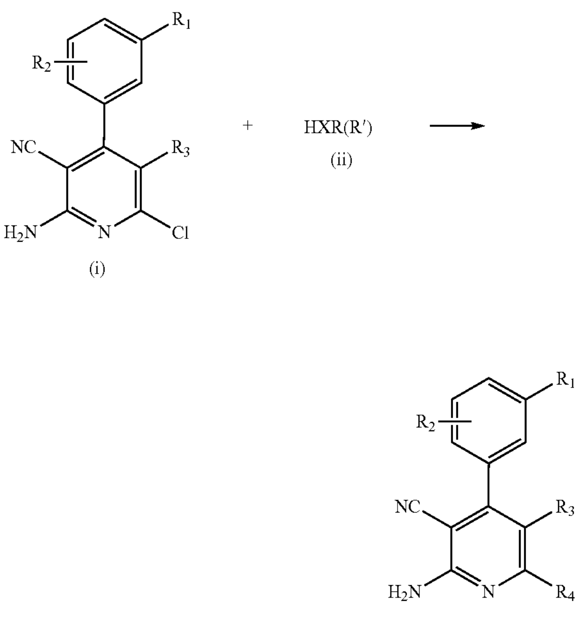

(i) (ii) (I)

Scheme 1 represents the preparation of compounds of the invention in a single-step procedure by substitution of cyanopyridines of formula (i) by commercial or synthetic nucleophiles of formula (ii), wherein X, R and R' are as defined herein, in the presence of a base such as trimethylamine in an aprotic solvent such as THF. The synthesis of the cyanopyridines of formula (i) is well documented in the literature and can be prepared following two-step protocols described by Murray et al., 1995 (*Tetrahedron,* 1995, 51, 635, DOI: 10.1016/0040-4020(94)00922-H) or Piper et al., 1986 (*J. Med. Chem.,* 29, 1080, DOI: 10.1021jm00156a029) or one-pot protocol such as described by Duindam et al., 1993 (*Synthetic Commun.,* 23, 2605, DOI: 10.1080/00397919308012595).

Scheme 2

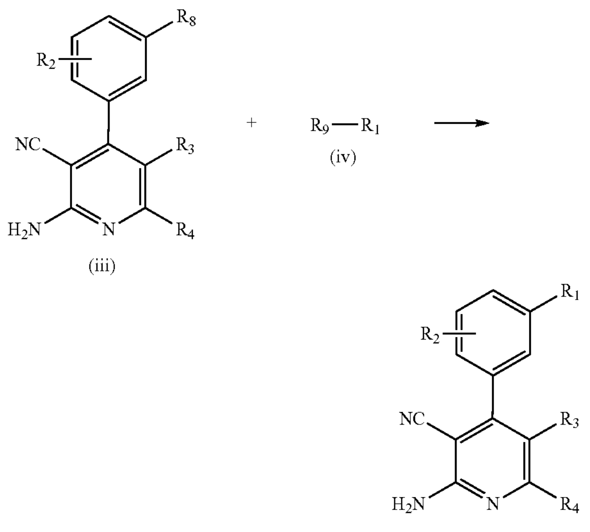

(iii) (iv) (I)

Scheme 2 represents the cross-coupling of the intermediates of formula (iii) and (iv), wherein $R_1$, $R_2$, $R_3$ and $R_4$ are as defined above and $R_8$ and $R_9$ are selected from halogeno, boronic acid or boronic pinacol ester group, in presence of a mineral base (such as $K_2CO_3$) and a source of palladium in catalytic amount (such as palladium(II) dichloride or tetrakis(triphenylphosphine)palladium(0)). This cross-coupling step can be performed under thermal conditions in apolar solvents like toluene, also called by thermal activation (such as described in Pan et al., 2008, *Catal. Commun.,* 9, 508-510) or under microwaved irradiation in polar solvents (such as methanol, water . . . ).

Scheme 3

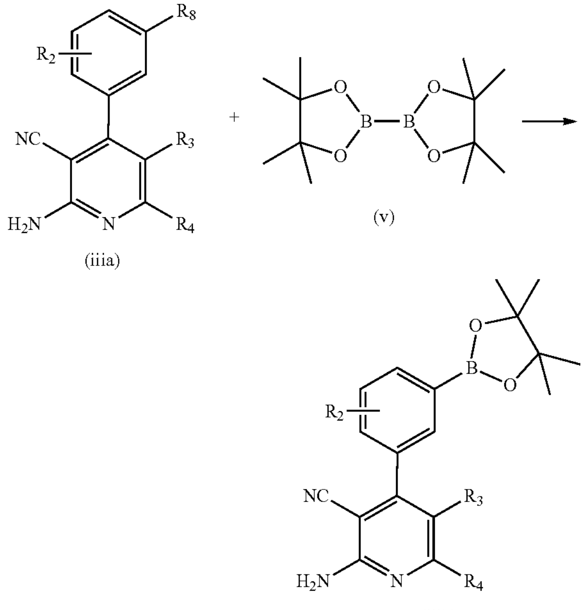

(iiia) (v) (iiib)

Scheme 3 presents a specific example of Scheme 2 for the synthesis of the intermediate of formula (iiib) by cross-coupling reaction between the bromoaryl of formula (iiia), wherein $R_2$, $R_3$ and $R_4$ are as defined above, and commercial bis(pinacolato)diboron of formula (v) under thermal activation of microwave irradiation as described in Scheme 2.

Scheme 4

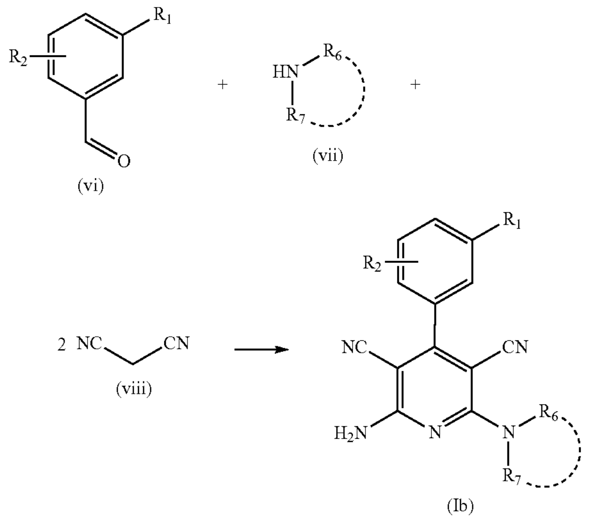
(vi) (vii) (viii) (Ib)

Scheme 4 illustrates the preparation of compounds (Ib) in a single-step procedure by cyclization of cyanopyridines from commercial or synthesized aldehydes of formula (vi) in the presence of cyclic amine of formula (vii), wherein $R_1$ and $R_2$ are as described above and $R_6$ and $R_7$ form together an optionally substituted heterocyclic alkyl as defined herein, two equivalents of malononitrile (viii), an eventual catalyst (such as 4-(Dimethylamino)pyridine (4-DMAP)) and an oxidizing agent (such as air) in a polar protic solvent (such as methanol).

Scheme 5

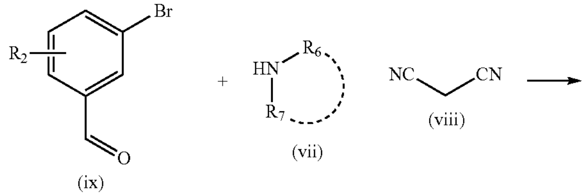
(ix) (vii) (viii)

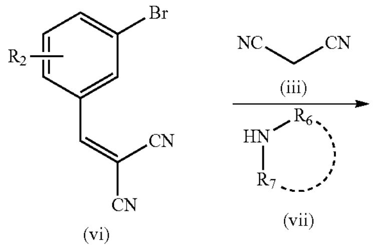
(vi) (iii) (vii)

-continued

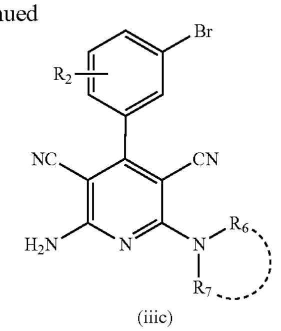
(iiic)

Scheme 5 illustrates the preparation of an intermediate compound of formula (iiic) in a two-step manner. First, the synthesis of the intermediate of formula (vi) can be achieved from the reaction of commercial bromobenzaldehyde of formula (ix) in the presence of one equivalent of malononitrile (viii), an eventual catalytic amount of a cyclic amine of formula (vii), wherein $R_2$ are as described above and $R_6$ and $R_7$ form together an optionally substituted heterocyclic alkyl as defined herein, and an oxidizing agent (such as air) in a polar protic solvent (such as methanol). The isolated intermediate (vi) can be further reacted in the presence of one equivalent of malononitrile (iii) and one equivalent of amine of formula (vii).

This two-step approach is more adapted to obtain gram-quantities.

Compounds (iiic), as described above, are a specific example of compound (iiia) and can therefore be used in the synthesis of compounds of the invention (I) following the procedure presented Scheme 3.

EXAMPLES

The following abbreviations refer respectively to the definitions below: CV (Column dead-volume); cyclo (cyclohexane); DCM (dichloromethane); DHP (2,4-dihydropyrane); DMF (dimethylformamide); eq. (Equivalents (mol %)); ESI (Electrospray ionization); HRMS (High-resolution mass spectrum); NMR (Nuclear Magnetic Resonance); PBS (phosphate-buffered saline); r.t. (room temperature); TFA (Trifluoroacetic acid); TLC (Thin layer chromatography); TOF (Time Of Flight); UPLC (Ultra-high performance liquid chromatography); UV (Ultraviolet).

Example 1: Synthesis of Compounds of the Invention

Compounds of the invention were prepared according to Schemes 1 to 5 as follows.

General experimental: Unless otherwise noted, all products were obtained from commercial sources and used without further purification. Anhydrous solvents such as methanol, DMF or toluene were purchased over molecular sieve, closed by AcroSeal®.

All preparative columns were performed by flash chromatography on a Buchi Pure C-815 Flash system with a UV detector. The corresponding PureFlash ID cartridges (4 g, 12 g, 24 g, 40 g or 120 g, amorphous silica, 35-45 μm mesh) were the purchased from Buchi and the flow rates were set according to the preset parameters (15, 30, 32, 45 & 85 mL/min respectively). Samples were loaded as solid deposit prepared with amorphous silica 40-60 μm mesh.

All described yields are isolated yields unless stated otherwise.

The $^{1}H$ NMR spectra were recorded on a Bruker 600 MHz spectrometer equipped with a cryoprobe and are calibrated on the residual protiated solvent. The $^{13}C$ NMR spectra were recorded at 125 MHz and the solvent resonance is used as internal standard. Both $^{1}H$ NMR and $^{13}C$ NMR chemical shifts are reported in parts per million downfield from tetramethylsilane. Low resolution mass spectra were recorded on an Advion PressionL, coupled to an ESI source, operating in positive and negative ion mode simultaneously. HRMS were recorded on a Xevo G2 TOF, coupled to an ESI source, operating either in positive or in negative acquisition mode.

Small Scale, One-Pot Cyanopyridine Cyclization According to Scheme 4

In a small round-bottom flask equipped with a stirrer, an aldehyde of formula (vi) (1 eq.) and malononitrile (viii) (1 eq.) were solubilized in methanol (0.2 M) (solution A). The solution A was vigorously stirred right away. In case the aldehyde contains a basic site (e.g., pyridine), no catalyst is needed. Else, in a small vial, a solution of cyclic amine of formula (vii) (1.2 eq.) in MeOH (0.2 M) was prepared (solution B). A drop or two of the solution B was added to the solution A. After stirring 30 min at r.t., more malononitrile (viii) (1 eq.) was added followed by dropwise addition of the rest of solution B. The reaction was stirred at r.t., open to air until completion; completion was assessed by TLC (cyclo:EtOAc 8:2). The medium was diluted with DCM ($5\times V_{MeOH}$), silica was directly added on top of the mixture and the solvent was removed under reduced pressure. The crude was purified by flash chromatography (12 g cartridge for 0.5 to 1 mmol of starting aldehyde) with a cyclo:EtOAc gradient (95:5, 3 CV; 95:5→8:2, 12 CV; 8:2, 6 CV; methanol wash).

Gram-Scale Cyanopyridine Cyclization According to Scheme 5

In a mortar or the bowl of a mechanical stirring device, an aldehyde of formula (ix) (1.05 to 1.2 eq.) and malononitrile (viii) (1 eq.) were solubilized in MeOH (2 to 1 M) (solution A). The solution A was vigorously stirred right away. In case the aldehyde contains a basic site (e.g., pyridine), no catalyst is needed. Else, in a small vial, a solution of cyclic amine of formula (vii) in MeOH (0.1 M) was prepared (solution B). While stirring, the solution B was added dropwise to the solution A, up to 5 mol % of the amine. In less than 3 to 5 min, a thick white paste must form, stirring was kept for 5 to 30 min before addition of cold water. The precipitate was filtered, rinsed twice with cold water then rinsed three times with a minimum of cold ether. The powder was dried under reduced pressure for 16 h to 24 h, yielding intermediate (vi), used without further purification.

In a round-bottom flask, the obtained intermediate of formula (vi) (1 eq.) was suspended in MeOH (about 0.5 M). At 0° C., the addition of the malononitrile (viii) (1 eq.) was consecutively followed by dropwise addition of the cyclic amine of formula (vii) (1.2 eq.). The flask was closed by a guard filled with $CaCl_2$) beads (to allow air exchange) and stirred for 30 min at 0° C. then at r.t. until completion; completion was assessed by TLC (cyclo:EtOAc 8:2 or DCM:MeOH 9:1). The crude product was purified by flash chromatography.

Suzuki Cross-Coupling (Thermal Activation)

The used procedure was adapted from Pan et al., 2008, supra.

In a 25 mL round-bottom flask equipped with a magnetic stirrer, a commercial or synthetic bromoaryl (1 eq.), a boronic acid or boronic pinacol ester (2 eq.), potassium carbonate (3 eq.) and palladium(II) dichloride (0.05 eq.) were consecutively added to toluene (0.5 M). The mixture was stirred at 110° C. for 24 h, open to air. Completion was assessed by TLC (cyclo:DCM 8:2). Palladium and salts were removed by filtration on a celite pad, washed with DCM (2×5 mL). Finally, the solvents were removed under reduced pressure and the crude product purified by flash chromatography with a cyclo:DCM gradient.

Microwave-Assisted Suzuki Cross-Coupling

In a 2-5 mL microwave tube equipped with a magnetic stirrer a commercial or synthetic bromoaryl (1 eq.), a boronic acid or boronic pinacol ester (1.2 to 3 eq.) and potassium carbonate (3 eq.) were solubilized in a $THF:H_2O$ 2:1 mixture (0.05 M). The solution was bubbled with argon for 10 min before addition of tetrakis(triphenylphosphine) palladium(0) (0.05 eq.). The tube was sealed and heated at 80° C. or 100° C. for 15 to 30 min under microwave irradiation. The medium was diluted with water and the crude product was extracted by EtOAc×3. The organic phases were combined, washed with brine, dried over $MgSO_4$ and the solvent was removed under reduced pressure. The crude product was purified by flash chromatography (4 g cartridge for less than 0.5 mmol of starting bromoaryl) with a cyclo:MixA[toluene:acetone 8:2 mixture] gradient (5:5, 6 CV; 5:5→0:10, 6 CV; 0:10, 6 CV; methanol wash).

Intermediates of Formula (i)

4-([1,1'-biphenyl]-3-yl)-2-amino-6-chloropyridine-3,5-dicarbonitrile (Wherein $R_1$ is Phenyl, $R_2$ is a Hydrogen and $R_3$ is a Cyano)

(ia)

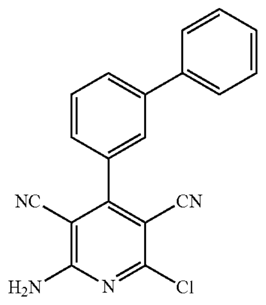

The intermediate was prepared following a two-step protocol described by Murray et al., 1995 (*Tetrahedron,* 1995, 51, 635, DOI: 10.1016/0040-4020(94)00922-H) starting from 3-(trimethoxymethyl)-1,1'-biphenyl (1.29 g, 5.0 mmol, 1 eq.) and was isolated as crude powder (650 mg, 2.0 mmol, 39% isolated yield). $^{1}H$ NMR (600 MHz, $(CD_3)_2SO$) δ 7.91 (d, J=1.8 Hz, 1H), 7.90 (dt, J=7.7, 1.5 Hz, 1H), 7.75-7.71 (m, 2H), 7.68 (t, J=7.7 Hz, 1H), 7.59 (dt, J=7.7, 1.5 Hz, 1H), 7.52 (t, J=7.7 Hz, 2H), 7.45-7.39 (m, 1H). $^{13}C$ NMR (151 MHz, $(CD_3)_2SO$) δ 160.3, 160.2, 155.3, 140.5, 139.1, 134.1, 129.5, 129.1, 128.9, 128.0, 127.5, 127.0, 126.9, 115.2, 114.5, 96.3, 89.8. MS ($ESI^-$) calculated for $C_{19}H_{11}N_4Cl$: $[M-H^+]$ m/z=329.1, found m/z=329.3.

Intermediates of Formula (vi)

4'-methyl-[1,1'-biphenyl]-3-carbaldehyde (Wherein $R_1$ is 4-Methylphenyl and $R_2$ is a Hydrogen)

(via)

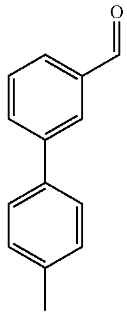

The intermediate was prepared as described above by thermal activation starting from 3-bromobenzaldehyde (0.12 mL, 1.0 mmol, 1 eq.) and p-tolylboronic acid (202 mg, 1.5 eq.) and was isolated as a translucent oil (113 mg, 0.58 mmol, 58% isolated yield). $^1$H NMR (600 MHz, $CDCl_3$) δ 10.09 (s, 1H), 8.09 (t, J=1.8 Hz, 1H), 7.86-7.83 (m, 2H), 7.60 (t, J=7.6 Hz, 1H), 7.56-7.51 (m, 2H), 7.32-7.27 (m, 2H), 2.42 (s, 3H). $^{13}$C NMR (151 MHz, $CDCl_3$) δ 192.6, 142.3, 138.1, 136.9, 133.0, 129.9, 129.6, 128.5, 128.1, 127.1, 21.3.

2'-fluoro-[1,1'-biphenyl]-3-carbaldehyde (Wherein $R_1$ is 2-Fluorophenyl and $R_2$ is a Hydrogen)

(vib)

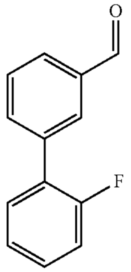

The intermediate was prepared as described above by thermal activation starting from 3-bromobenzaldehyde (0.12 mL, 1.0 mmol, 1 eq.) and 2-fluorophenylboronic acid (276 mg, 2 eq.) and was isolated as a translucent oil (135 mg, 0.68 mmol, 68% isolated yield). $^1$H NMR (600 MHz, $CDCl_3$) δ 10.09 (s, 1H), 8.06 (q, J=1.9 Hz, 1H), 7.90 (dt, J=7.7, 1.4 Hz, 1H), 7.83 (dtd, J=7.7, 1.7, 1.2 Hz, 1H), 7.62 (t, J=7.7 Hz, 1H), 7.48 (td, J=7.7, 1.8 Hz, 1H), 7.38 (dddd, J=8.3, 7.4, 5.0, 1.8 Hz, 1H), 7.25 (td, J=7.5, 1.2 Hz, 1H), 7.19 (ddd, J=10.8, 8.3, 1.2 Hz, 1H). $^{13}$C NMR (151 MHz, $CDCl_3$) δ 192.3 (d, J=1.5 Hz), 160.7, 159.1, 136.9 (d, J=22.7 Hz), 135.1 (d, J=3.3 Hz), 130.8 (d, J=3.2 Hz), 130.5 (d, J=2.8 Hz), 129.9 (d, J=8.2 Hz), 129.3, 128.9, 127.8 (d, J=13.1 Hz), 124.8 (d, J=3.7 Hz), 116.4 (d, J=22.5 Hz).

3'-fluoro-[1,1'-biphenyl]-3-carbaldehyde (Wherein $R_1$ is 3-Fluorophenyl and $R_2$ is a Hydrogen)

(vic)

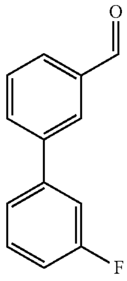

The intermediate was prepared as described above by thermal activation starting from 3-bromobenzaldehyde (0.12 mL, 1.0 mmol, 1 eq.) and 3-fluorophenylboronic acid (276 mg, 2 eq.) and was isolated as a translucent oil (154 mg, 0.77 mmol, 77% isolated yield). $^1$H NMR (600 MHz, $CDCl_3$) δ 10.10 (s, 1H), 8.11-8.06 (m, 1H), 7.89 (dt, J=7.6, 1.4 Hz, 1H), 7.84 (ddd, J=7.7, 2.0, 1.2 Hz, 1H), 7.63 (t, J=7.6 Hz, 1H), 7.46-7.40 (m, 2H), 7.33 (ddd, J=9.9, 2.6, 1.7 Hz, 1H), 7.13-7.08 (m, 1H). $^{13}$C NMR (151 MHz, $CDCl_3$) δ 192.2 (d, J=1.8 Hz), 163.4 (d, J=246.2 Hz), 142.1 (d, J=7.7 Hz), 141.1 (d, J=2.3 Hz), 137.2, 133.1, 130.7 (d, J=8.4 Hz), 129.8, 129.4, 128.2, 123.0 (d, J=3.0 Hz), 115.0 (d, J=21.1 Hz), 114.3 (d, J=22.2 Hz).

4'-fluoro-[1,1'-biphenyl]-3-carbaldehyde (Wherein $R_1$ is 4-Fluorophenyl and $R_2$ is a Hydrogen)

(vid)

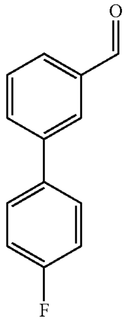

The intermediate was prepared as described above by thermal activation starting from 3-bromobenzaldehyde (0.12 mL, 1.0 mmol, 1 eq.) and 4-fluorophenylboronic acid (276 mg, 2 eq.) and was isolated as a translucent oil (115 mg, 0.58 mmol, 58% isolated yield). $^1$H NMR (600 MHz, $CDCl_3$) δ 10.09 (s, 1H), 8.06 (t, J=1.8 Hz, 1H), 7.86 (dt, J=7.6, 1.4 Hz, 1H), 7.82 (ddd, J=7.7, 2.0, 1.2 Hz, 1H), 7.63-7.57 (m, 3H), 7.19-7.14 (m, 2H). $^{13}$C NMR (151 MHz, $CDCl_3$) δ 192.4 (d, J=2.0 Hz), 163.0 (d, J=247.7 Hz), 141.4, 137.1, 136.0 (d, J=3.2 Hz), 133.0, 129.7, 129.0, 128.9, 128.0, 116.1 (d, J=21.7 Hz).

3-(2-(tetrahydro-2H-pyran-2-yl)-2H-tetrazol-5-yl) benzaldehyde (Wherein $R^1$ is 2-(tetrahydro-2H-pyran-2-yl)-2H-tetrazol-5-yl and $R_2$ is a Hydrogen)

(vie)

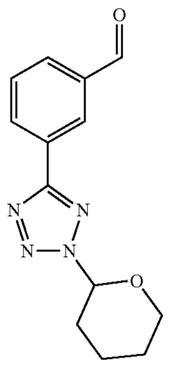

The intermediate 3-(tetrazol-5-yl)benzaldehyde can be prepared according to the literature (Bianchini et al., 2021, *Med. Chem.*, 64, 16820-16837). Then, in a dry 25 mL round bottom flask equipped with a magnetic stirrer and a condenser, DHP (0.18 mL, 2 eq.) was solubilized in dry toluene (5 mL) and mixed with a solution of 3-(tetrazol-5-yl) benzaldehyde (174 mg, 1.0 mmol, 1 eq.) in dry DMF (0.79 mL). The TFA (0.008 mL, 0.1 eq.) was added dropwise. The flask was purged with argon and heated at 110° C. for 24 h. The completion of the reaction was assessed by TLC (Rf=0.57 in DCM:MeOH 98:2) before being stopped by addition of $Na_2CO_3$ 10% in water (10 mL) and water (20 mL). The crude product was extracted by EtOAc (3×15 mL) and the organic phases were combined, washed with brine (20 mL), dried over $MgSO_4$ and the solvents were removed under reduced pressure. The purification was done by flash chromatography on a 12 g silica cartridge with a cyclo:DCM gradient (8:2, 3 CV; 8:2→0:10, 6 CV; methanol wash) and isolated as an oil (66 mg, 0.26 mmol, 26% isolated yield). $^1H$ NMR (600 MHz, $CDCl_3$) δ 10.11 (s, 1H), 8.70 (t, J=1.8 Hz, 1H), 8.47 (dt, J=7.7, 1.5 Hz, 1H), 8.01 (dt, J=7.7, 1.4 Hz, 1H), 7.68 (t, J=7.7 Hz, 1H), 6.10 (dd, J=7.6, 2.9 Hz, 1H), 4.08-4.02 (m, 1H), 3.88-3.80 (m, 1H), 2.57-2.46 (m, 1H), 2.25-2.15 (m, 2H), 1.88-1.71 (m, 3H). $^{13}C$ NMR (151 MHz, $CDCl_3$) δ 191.81, 164.1, 137.1, 132.7, 130.8, 129.9, 129.0, 128.6, 88.2, 67.1, 29.2, 24.7, 20.9. MS ($ESI^+$) calculated for $C_{13}H_{14}N_4O_2$: $[M+Cl^-]$ m/z=293.1, found m/z=293.1.

Intermediates of Formula (iv)

3-bromo-1-(tetrahydro-2H-pyran-2-yl)-1H-pyrazole (Wherein $R_1$ is 1-(tetrahydro-2H-pyran-2-yl)-1H-pyrazole and $R_9$ Bromo)

(iva)

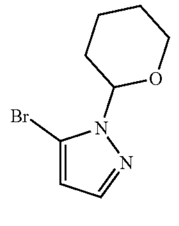

In a 25 mL round bottom flask equipped with a stirrer and a condenser, DHP (0.55 mL, 2 eq.) was solubilized in anhydrous toluene (3 mL). The flask was flushed with argon before slow addition of TFA (0.023 mL, 0.1 eq.) and pyrazole (204 mg, 3 mmol, 1 eq.). The solution was heated at 100° C. for 16 h. Completion was assessed by TLC, revealed with basic $KMnO_4$ (Rf=0.18 in cyclo:EtOAc 8:2). The reaction was quenched with aq. NaOH 0.5 M (20 mL) and the crude intermediate was extracted by EtOAc (3×15 mL). The organic phases were combined, washed with brine (20 mL), dried over $MgSO_4$ and the solvents were removed under reduced pressure. The 1-(tetrahydro-2H-pyran-2-yl)-1H-pyrazole intermediate (not drawn) was purified by flash chromatography on a 12 g silica cartridge with a cyclo: EtOAc gradient (9:1, 3 CV; 9:1→8:2, 3 CV; 8:2, 3 CV; methanol wash) and isolated as a translucent oil (421 mg, 2.8 mmol, 92% isolated yield). The 3-bromo-1-(tetrahydro-2H-pyran-2-yl)-1H-pyrazole intermediate (va) was prepared from the 1-(tetrahydro-2H-pyran-2-yl)-1H-pyrazole intermediate (410 mg, 2.7 mmol, 1 eq.) following a literature protocol (Nicolaou et al., 2015, *ChemMedChem.*, 10, 1974-1979) and isolated as a light-yellow oil (460 mg, 2.0 mmol, 74% isolated yield). $^1H$ NMR (600 MHz, $CDCl_3$) δ 7.50 (d, J=2.4 Hz, 1H), 6.31 (d, J=2.5 Hz, 1H), 5.32 (dd, J=9.3, 2.9 Hz, 1H), 4.07-4.03 (m, 1H), 3.68 (td, J=11.1, 2.8 Hz, 1H), 2.11-2.00 (m, 2H), 1.70-1.65 (m, 3H), 1.63-1.58 (m, 1H). $^{13}C$ NMR (151 MHz, $CDCl_3$) δ 129.8, 126.5, 109.1, 87.9, 67.9, 30.5, 25.0, 22.3.

Intermediates of Formula (Iiia)

2-amino-4-(3-bromophenyl)-6-(piperidin-1-yl)pyridine-3,5-dicarbonitrile (Wherein $R_2$ is a Hydrogen, $R_3$ is Cyano and $R_4$ is Piperidine)

(iiiaa)

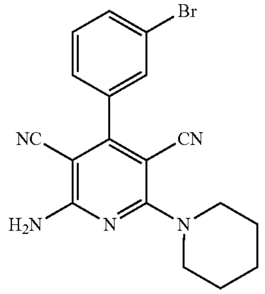

In a 100 mL round-bottom flask equipped with a stirrer, 3-bromobenzaldehyde (925 mg, 5 mmol, 1 eq.) and malononitrile (viii) (330 mg, 1 eq.) were solubilized in methanol (10 mL) (solution A). The solution A was vigorously stirred right away. A solution of piperidine (0.59 mL, 1.2 eq.) in MeOH (5 mL) was prepared (solution B) and added dropwise over 1 h to the solution A. More malononitrile (viii) (330 mg, 1 eq.) solubilized in MeOH (5 mL) was added and the reaction was stirred at r.t., open to air until completion. Completion was assessed by TLC (Rf=0.16 cyclo:EtOAc 8:2). The medium was diluted with DCM (20 mL), silica was directly added on top of the mixture and the solvent was removed under reduced pressure. The crude was purified by flash chromatography on a 24 g cartridge with a cyclo: EtOAc gradient (9:1, 3 CV; 9:1→8:2, 6 CV; 8:2, 8 CV; methanol wash). $^1H$ NMR (600 MHz, $CDCl_3$) δ 7.65 (dt, J=7.3, 1.9 Hz, 1H), 7.61 (t, J=1.8 Hz, 1H), 7.43-7.36 (m, 2H), 5.50 (s, 2H), 3.84-3.79 (m, 4H), 1.76-1.68 (m, 6H). $^{13}C$ NMR (151 MHz, $CDCl_3$) δ 160.9, 160.5, 159.3, 136.8, 133.7, 131.6, 130.6, 127.4, 122.9, 117.3, 116.1, 83.6, 81.8, 49.5, 26.1, 24.5. MS ($ESI^+$) calculated for $C_{18}H_{16}N_5Br$: $[M+H^+]$ m/z=382.1 & 384.1, found m/z=382.1 & 384.1. HRMS ($ESI^+$) calculated for $C_{18}H_{16}N_5Br$: $[M+H^+]$ m/z=382.0662, found m/z=382.0667.

2-amino-4-(3-bromo-2-fluorophenyl)-6-(piperidin-1-yl)pyridine-3,5-dicarbonitrile (Wherein $R_2$ is a 2-Fluoro, $R_3$ is Cyano and $R_4$ is Piperidine)

(iiiab)

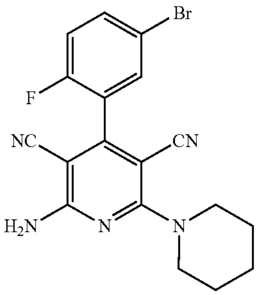

In a small round-bottom flask equipped with a stirrer, 5-bromo-2-fluorobenzaldehyde (317 mg, 1.56 mmol, 1 eq.) and malononitrile (viii) (264 mg, 2.6 eq.) were solubilized in methanol (5 mL) (solution A). The solution A was vigorously stirred right away. A solution of piperidine (0.24 mL, 1.5 eq.) in MeOH (1 mL) was prepared (solution B) and a few drops were added to the solution A. After stirring 30 min at r.t., the rest of solution B was slowly added. The reaction was stirred at r.t., open to air until completion. The medium was diluted with water (10 mL) and brine (10 mL) and the crude product extracted by AcOEt (3×15 mL). The organic phases were combined, dried with $MgSO_4$ and the solvent was removed under reduced pressure. The crude was purified by flash chromatography on a 12 g silica cartridge with a cyclo:DCM gradient (8:2, 4 CV; 8:2→4:6, 8 CV; 4:6, 4 CV; methanol wash) and isolated as a white powder (63 mg, 0.16 mmol, 10% isolated yield). $^{1}H$ NMR (600 MHz, $CDCl_3$) δ 7.60 (ddd, J=8.9, 4.5, 2.5 Hz, 1H), 7.49 (dd, J=6.3, 2.5 Hz, 1H), 7.13 (t, J=9.0 Hz, 1H), 5.39 (s, 2H), 3.84-3.80 (m, 4H), 1.73-1.68 (m, 6H). $^{13}C$ NMR (151 MHz, $CDCl_3$) δ 160.2, 159.1, 158.2 (d, J=250.9 Hz), 155.2, 135.4 (d, J=8.4 Hz), 133.1 (d, J=2.1 Hz), 124.8 (d, J=16.8 Hz), 118.4 (d, J=23.0 Hz), 117.2 (d, J=3.6 Hz), 116.9, 115.7, 84.3, 82.3, 49.2, 26.1, 24.5. MS ($ESI^+$) calculated for $C_{18}H_{15}N_5FBr$: $[M+H^+]$ m/z=400.1 & 402.1, found m/z=400.4 & 402.3.

2-amino-4-(3-bromo-2-fluorophenyl)-6-(piperidin-1-yl)pyridine-3,5-dicarbonitrile (Wherein $R_2$ is a 2-Fluoro, $R_3$ is Cyano and $R_4$ is Piperidine)

(iiiac)

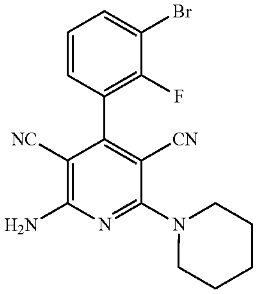

In a small round-bottom flask equipped with a stirrer, 3-bromo-2-fluorobenzaldehyde (317 mg, 1.56 mmol, 1 eq.) and malononitrile (viii) (264 mg, 2.6 eq.) were solubilized in methanol (5 mL) (solution A). The solution A was vigorously stirred right away. A solution of piperidine (0.24 mL, 1.2 eq.) in MeOH (1 mL) was prepared (solution B) and a few drops were added to the solution A. After stirring 30 min at r.t., the rest of solution B was slowly added. The reaction was stirred at r.t., open to air until completion. The medium was diluted with water (10 mL) and brine (10 mL) and the crude product extracted by AcOEt (3×15 mL). The organic phases were combined, dried with $MgSO_4$ and the solvent was removed under reduced pressure. The crude was purified by flash chromatography on a 12 g silica cartridge with a cyclo:DCM gradient (8:2, 4 CV; 8:2→4:6, 8 CV; 4:6, 4 CV; methanol wash) and isolated as a white powder (63 mg, 0.16 mmol, 10% isolated yield). $^{1}H$ NMR (600 MHz, $CDCl_3$) δ 7.70 (ddd, J=8.1, 6.4, 1.6 Hz, 1H), 7.32 (ddd, J=7.9, 6.2, 1.6 Hz, 1H), 7.18 (t, J=7.8 Hz, 1H), 5.38 (s, 2H), 3.84-3.78 (m, 4H), 1.76-1.66 (m, 6H). $^{13}C$ NMR (151 MHz, $CDCl_3$) δ 160.2, 159.1, 155.6, 155.5 (d, J=250.8 Hz), 135.8, 129.5 (d, J=2.1 Hz), 125.6 (d, J=4.2 Hz), 124.2 (d, J=16.2 Hz), 116.8, 115.7, 110.3 (d, J=20.9 Hz), 84.2, 82.2, 49.1, 26.0, 24.4. MS ($ESI^+$) calculated for $C_{18}H_{15}N_5FBr$: $[M+H^+]$ m/z=400.1 & 402.1, found m/z=400.3 & 402.3.

2-amino-4-(3-chloro-5-fluorophenyl)-6-(piperidin-1-yl)pyridine-3,5-dicarbonitrile (Wherein $R_2$ is a 5-Fluoro, $R_3$ is Cyano and $R_4$ is Piperidine)

(iiiad)

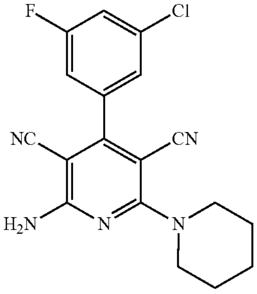

In a small round-bottom flask equipped with a stirrer, 3-chloro-5-fluorobenzaldehyde (317 mg, 2 mmol, 1 eq.) and malononitrile (viii) (264 mg, 2 eq.) were solubilized in methanol (6 mL). The solution was vigorously stirred right away and cooled to 0° C. Piperidine (0.24 mL, 1.2 eq.) in MeOH (1 mL) was slowly added. The reaction was stirred at r.t., open to air until completion. The medium was diluted with brine (20 mL) and the crude product extracted by AcOEt (3×15 mL). The organic phases were combined, dried with $MgSO_4$ and the solvent was removed under reduced pressure. The crude was purified by flash chromatography on a 24 g silica cartridge with a cyclo:EtOAc isocratic gradient (85:15, 12 CV; methanol wash) and isolated as a white powder (136 mg, 0.38 mmol, 19% isolated yield). $^1H$ NMR (600 MHz, $CDCl_3$) δ 7.26-7.22 (m, 2H), 7.09 (dt, J=8.1, 1.7 Hz, 1H), 5.51 (s, 2H), 3.84-3.80 (m, 4H), 1.73-1.67 (m, 6H). $^{13}C$ NMR (151 MHz, $CDCl_3$) δ 163.4, 161.8, 160.3, 159.73, 159.71, 159.2, 137.8, 137.7, 136.1, 136.0, 124.91, 124.89, 118.5, 118.3, 117.0, 115.8, 114.7, 114.6, 83.3, 81.6, 49.4, 26.1, 24.4. MS ($ESI^+$) calculated for $C_{18}H_{15}N_5FCl$: [$M+H^+$] m/z=356.1, found m/z=356.4.

Intermediates of Formula (Iiib)

(3-(2-amino-3,5-dicyano-6-(piperidin-1-yl)pyridin-4-yl)phenyl)boronic acid pinacol ester (Wherein $R_2$ is a Hydrogen, $R_3$ is Cyano and $R_4$ is Piperidine)

(iiiba)

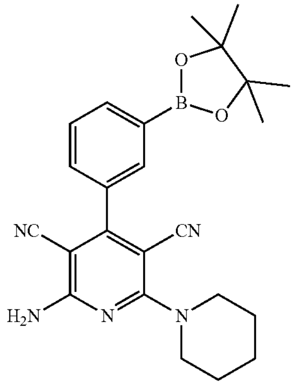

In a 25 mL round-bottom flask purged with argon and equipped with a magnetic stirrer, 2-amino-4-(3-bromophenyl)-6-(piperidin-1-yl)pyridine-3,5-dicarbonitrile (iiiaa) (382 mg, 1 mmol, 1 eq.) and bis(pinacolato)diboron (v) (303 mg, 1.2 eq) were solubilized in degassed toluene (10 mL). The potassium carbonate (414 mg, 3 eq.) and tetrakis (triphenylphosphine)palladium(0) (58 mg, 0.05 eq.) were added at the same time and the medium was heated at 110° C. for 16 h. Completion was assessed by TLC (Rf=0.06 in cyclo:DCM 4:6). The palladium and salts were removed by filtration on a celite pad, washed with EtOAc (3×5 mL) and the solvents were removed under reduced pressure. The product purified by flash chromatography on a 12 g cartridge with a cyclo:DCM gradient (5:5, 6 CV; 5:5→0:10, 6 CV; 0:10, 9 CV; methanol wash) and isolated as an off-white powder (213 mg, 0.5 mmol, 50% isolated yield). $^1H$ NMR (600 MHz, $CDCl_3$) δ 7.94 (dt, J=7.3, 1.3 Hz, 1H), 7.87 (dt, J=1.9, 0.8 Hz, 1H), 7.54 (dt, J=7.7, 1.7 Hz, 1H), 7.50 (t, J=7.5 Hz, 1H), 5.33 (s, 2H), 3.82-3.77 (m, 2H), 1.72-1.66 (m, 5H), 1.35 (s, 12H). $^{13}C$ NMR (151 MHz, $CDCl_3$) δ 162.9, 160.7, 159.2, 137.0, 134.8, 134.4, 131.2, 128.3, 117.5, 116.3, 84.2, 82.1, 49.5, 27.1, 26.2, 25.1, 24.5. MS ($ESI^+$) $C_{24}H_{28}N_5O_2B$: [$M+H^+$] m/z=430.2, found m/z=430.4.

Compounds of Formula (I)

4-([1,1'-biphenyl]-3-yl)-2-amino-6-(azetidin-1-yl)pyridine-3,5-dicarbonitrile (1) (Wherein $R_1$ is Phenyl, $R_2$ is a Hydrogen, $R_3$ is Cyano and $R_4$ is Azetidine)

(1)

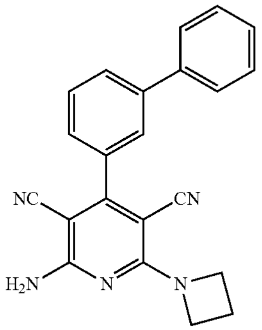

The product was prepared following the general procedure under Scheme 4 starting from commercial [1,1'-biphenyl]-3-carbaldehyde (55 mg, 0.30 mmol, 1 eq.) (intermediate of formula (vi) wherein $R_1$ is phenyl and $R_2$ is a hydrogen) and azetidine (0.024 mL, 1.2 eq.) (cyclo amine of formula (vii)) and was isolated as an off-white powder (27 mg, 0.08 mmol, 26% isolated yield). $^1H$ NMR (600 MHz, $CDCl_3$) δ 7.71 (ddd, J=7.7, 1.8, 1.1 Hz, 1H), 7.68 (t, J=1.8 Hz, 1H), 7.64-7.61 (m, 2H), 7.57 (t, J=7.7 Hz, 1H), 7.47-7.44 (m, 3H), 7.38-7.35 (m, 1H), 5.42 (s, 2H), 4.47-4.39 (m, 4H), 2.40 (tdd, J=8.8, 7.2, 6.0 Hz, 2H). $^{13}C$ NMR (151 MHz, $CDCl_3$) δ 161.0, 160.1, 159.3, 142.0, 140.6, 134.8, 129.40, 129.37, 129.0, 127.8, 127.6, 127.6, 127.4, 117.2, 116.9, 81.0, 80.6, 27.1, 16.3. MS ($ESI^+$) calculated for $C_{22}H_{17}N_5$: [$M+H^+$] m/z=352.2, found m/z=352.0. HRMS ($ESI^+$) calculated for $C_{22}H_{17}N_5$: [$M+H^+$] m/z=352.1557, found m/z=352.1575.

4-([1,1'-biphenyl]-3-yl)-2-amino-6-(pyrrolidin-1-yl)pyridine-3,5-dicarbonitrile (2) (Wherein $R_1$ is Phenyl, $R_2$ is a Hydrogen, $R_3$ is Cyano and $R_4$ is Pyrrolidine)

(2)

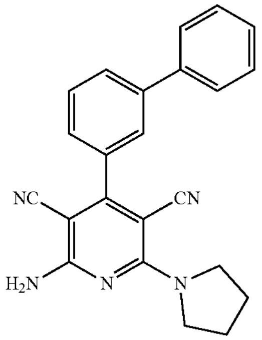

The product was prepared following the general procedure under Scheme 4 starting from commercial [1,1'-biphenyl]-3-carbaldehyde (intermediate of formula (vi) wherein $R_1$ is phenyl and $R_2$ is a hydrogen) (55 mg, 0.30 mmol, 1 eq.) and pyrrolidine (0.030 mL, 1.2 eq.) (cyclo amine or formula (vii)) and was isolated as an off-white powder (19 mg, 0.05 mmol, 17% isolated yield). $^1$H NMR (600 MHz, $CDCl_3$) δ 7.71 (dt, J=7.8, 1.5 Hz, 1H), 7.69 (t, J=1.8 Hz, 1H), 7.65-7.62 (m, 2H), 7.58 (t, J=7.6 Hz, 1H), 7.48-7.44 (m, 3H), 7.36 (t, J=7.4 Hz, 1H), 5.42 (s, 2H), 3.87-3.82 (m, 4H), 2.03-1.95 (m, 4H). $^{13}$C NMR (151 MHz, $CDCl_3$) δ 162.2, 159.4, 157.5, 141.9, 140.7, 135.4, 129.33, 129.30, 129.0, 127.8, 127.6, 127.5, 118.4, 116.9, 82.2, 81.2, 49.9, 27.1. MS (ESI$^+$) calculated for $C_{23}H_{19}N_5$: [M+H$^+$] m/z=366.2, found m/z=366.0. HRMS (ESI$^+$) calculated for $C_{23}H_{19}N_5$: [M+H$^+$] m/z=366.1714, found m/z=366.1706.

4-([1,1'-biphenyl]-3-yl)-2-amino-6-(piperidin-1-yl) pyridine-3,5-dicarbonitrile (3) (Wherein $R_1$ is Phenyl, $R_2$ is a Hydrogen, $R_3$ is Cyano and $R_4$ is Piperidine)

(3)

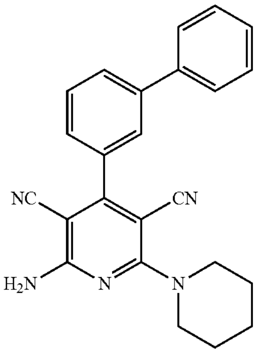

The product was prepared following Sarkar et al., 2014, *RSC Adv.*, 4, 53752-53760 starting from commercial [1,1'-biphenyl]-3-carbaldehyde (intermediate of formula (vi) wherein $R_1$ is phenyl and $R_2$ is a hydrogen) (0.080 mL, 0.5 mmol, 1 eq.) and was isolated as a white powder (13 mg, 0.03 mmol, 7% isolated yield). $^1$H NMR (600 MHz, $CDCl_3$) δ 7.73-7.70 (m, 2H), 7.66-7.62 (m, 2H), 7.58 (t, J=7.7 Hz, 1H), 7.49 (dt, J=7.7, 1.5 Hz, 1H), 7.45 (t, J=7.7 Hz, 2H), 7.37 (tt, J=7.4, 1.3 Hz, 1H), 5.49 (s, 2H), 3.86-3.80 (m, 4H), 1.73-1.70 (m, 6H). $^{13}$C NMR (151 MHz, $CDCl_3$) δ 162.4, 161.1, 159.5, 142.0, 140.6, 135.2, 129.5, 129.4, 129.0, 127.9, 127.8, 127.7, 127.6, 117.8, 116.6, 83.8, 81.9, 49.5, 26.2, 24.5. MS (ESI$^+$) calculated for $C_{24}H_{21}N_5$: [M+H$^+$] m/z=380.2, found m/z=380.1. HRMS (ESI$^+$) calculated for $C_{24}H_{21}N_5$: [M+H$^+$] m/z=380.1870, found m/z=380.1859.

2-amino-4-(2'-fluoro-[1,1'-biphenyl]-3-yl)-6-(piperidin-1-yl)pyridine-3,5-dicarbonitrile (4) (Wherein $R_1$ is 2-Fluorophenyl, $R_2$ is a Hydrogen, $R_3$ is Cyano and $R_4$ is Piperidine)

(4)

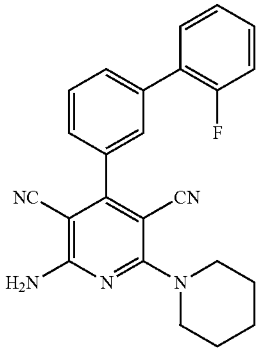

The product was prepared following Sarkar et al., 2014, supra starting from 2'-fluoro-[1,1'-biphenyl]-3-carbaldehyde (intermediate of formula (vib)) (100 mg, 0.5 mmol, 1 eq.) and was isolated as a white powder (45 mg, 0.11 mmol, 23% isolated yield). $^1$H NMR (600 MHz, $CDCl_3$) δ 7.72-7.67 (m, 2H), 7.59 (td, J=7.6, 0.7 Hz, 1H), 7.51 (dt, J=7.7, 1.5 Hz, 1H), 7.41 (td, J=4.4, 3.8, 2.8 Hz, 2H), 7.35-7.31 (m, 1H), 7.09-7.03 (m, 1H), 5.38 (s, 2H), 3.88-3.80 (m, 4H), 1.78-1.63 (m, 6H). $^{13}$C NMR (151 MHz, $CDCl_3$) δ 163.3 (d, J=246.0 Hz), 162.1, 161.3, 159.6, 142.8 (d, J=7.5 Hz), 140.7 (d, J=2.1 Hz), 135.5, 130.5 (d, J=8.4 Hz), 129.5 (d, J=26.6 Hz), 128.2, 127.9, 123.3, 117.9, 116.7, 114.6 (d, J=21.0 Hz), 114.4 (d, J=22.0 Hz), 83.7, 81.8, 49.4, 26.2, 24.6. MS (ESI$^+$) calculated for $C_{24}H_{20}N_5F$: [M+H$^+$] m/z=398.2, found m/z=398.8. HRMS (ESI$^+$) calculated for $C_{24}H_{20}N_5F$: [M+Na$^+$] m/z=420.1595, found m/z=420.1594.

2-amino-4-(3'-fluoro-[1,1'-biphenyl]-3-yl)-6-(piperidin-1-yl)pyridine-3,5-dicarbonitrile (5) (Wherein $R_1$ is 3-Fluorophenyl, $R_2$ is a Hydrogen, $R_3$ is Cyano and $R_4$ is Piperidine)

(5)

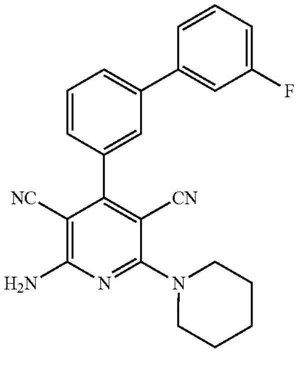

The product was prepared following Sarkar et al., 2014, supra starting from 3'-fluoro-[1,1'-biphenyl]-3-carbaldehyde (intermediate of formula (vic)) (100 mg, 0.5 mmol, 1 eq.) and was isolated as a white powder (34 mg, 0.08 mmol, 17% isolated yield). $^1$H NMR (600 MHz, $CDCl_3$) δ 7.71 (dq, J=7.7, 1.6 Hz, 1H), 7.68 (q, J=1.6 Hz, 1H), 7.58 (d, J=7.7 Hz, 1H), 7.55-7.49 (m, 2H), 7.37-7.30 (m, 1H), 7.23 (td, J=7.5, 1.2 Hz, 1H), 7.17 (ddd, J=10.9, 8.2, 1.2 Hz, 1H), 5.37 (s, 2H), 3.83-3.79 (m, 4H), 1.71 (t, J=3.1 Hz, 6H). $^{13}C$ NMR (151 MHz, $CDCl_3$) δ 162.0, 161.4, 159.9 (d, J=248.7 Hz), 159.6, 136.5, 135.1, 131.3 (d, J=3.3 Hz), 131.1 (d, J=3.2 Hz), 129.59 (d, J=1.1 Hz), 129.55 (d, J=4.0 Hz), 129.1, 128.1, 124.7 (d, J=3.6 Hz), 117.8, 116.7, 116.3 (d, J=22.5 Hz), 83.8, 81.8, 49.4, 26.1, 24.6. MS ($ESI^+$) calculated for $C_{24}H_{20}N_5F$: $[M+H^+]$ m/z=398.2, found m/z=398.8. HRMS ($ESI^+$) calculated for $C_{24}H_{20}N_5F$: $[M+Na^+]$ m/z=420.1595, found m/z=420.1594.

2-amino-4-(4'-fluoro-[1,1'-biphenyl]-3-yl)-6-(piperidin-1-yl)pyridine-3,5-dicarbonitrile (6) (Wherein $R_1$ is 4-Fluorophenyl, $R_2$ is a Hydrogen, $R_3$ is Cyano and $R_4$ is Piperidine)

(6)

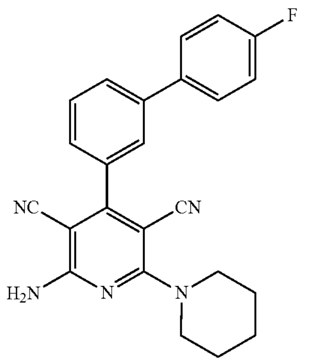

The product was prepared following Sarkar et al., 2014, supra starting from 4'-fluoro-[1,1'-biphenyl]-3-carbaldehyde (intermediate of formula (vid)) (100 mg, 0.5 mmol, 1 eq.) and was isolated as a white powder (34 mg, 0.08 mmol, 17% isolated yield). $^1H$ NMR (600 MHz, $CDCl_3$) δ 7.68-7.64 (m, 2H), 7.61-7.55 (m, 3H), 7.48 (dt, J=7.7, 1.5 Hz, 1H), 7.18-7.11 (m, 2H), 5.37 (s, 2H), 3.84-3.79 (m, 4H), 1.76-1.70 (m, 6H). $^{13}C$ NMR (151 MHz, $CDCl_3$) δ 162.9 (d, J=246.7 Hz), 162.2, 161.3, 159.6, 141.0, 136.8 (d, J=3.4 Hz), 135.4, 129.5, 129.3, 129.2 (d, J=8.2 Hz), 127.8 (d, J=19.2 Hz), 117.9, 116.8, 115.9 (d, J=21.5 Hz), 83.7, 81.8, 49.4, 26.2, 24.6. MS ($ESI^+$) calculated for $C_{24}H_{20}N_5F$: $[M+H^+]$ m/z=398.2, found m/z=398.8. HRMS ($ESI^+$) calculated for $C_{24}H_{20}N_5F$: $[M+Na^+]$ m/z=420.1595, found m/z=420.1594.

2-amino-4-(2'-methyl-[1,1'-biphenyl]-3-yl)-6-(piperidin-1-yl)pyridine-3,5-dicarbonitrile (7) (Wherein $R_1$ is 2-Methylphenyl, $R_2$ is a Hydrogen, $R_3$ is Cyano and $R_4$ is Piperidine)

(7)

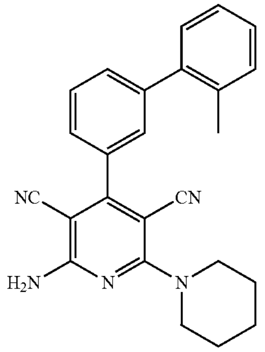

The product was prepared as described above by thermal activation starting from 2-amino-4-(3-bromophenyl)-6-(piperidin-1-yl)pyridine-3,5-dicarbonitrile (intermediate of formula (iiiaa)) (60 mg, 0.16 mmol, 1 eq.) and 2-methylphenylboronic acid (intermediate of formula (iv) wherein $R_1$ is 2-methylphenyl and $R_2$ is boronic acid) (63 mg, 3 eq.) and was isolated as a white powder (30 mg, 0.08 mmol, 49% isolated yield). $^1H$ NMR (600 MHz, $CDCl_3$) δ 7.55 (t, J=7.7 Hz, 1H), 7.47 (ddt, J=7.4, 5.8, 1.4 Hz, 2H), 7.43 (t, J=1.8 Hz, 1H), 7.32-7.25 (m, 2H), 5.35 (s, 2H), 3.83-3.76 (m, 4H), 2.32 (s, 3H), 1.86-1.66 (m, 6H). $^{13}C$ NMR (151 MHz, $CDCl_3$) δ 162.3, 161.3, 159.6, 142.7, 141.1, 135.8, 134.8, 131.4, 130.4, 130.1, 129.7, 128.7, 127.7, 127.3, 126.0, 117.8, 116.7, 83.9, 81.9, 49.4, 26.1, 24.6, 20.7. MS ($ESI^+$) calculated for $C_{24}H_{21}N_5$: $[M+H^+]$ m/z=394.2, found m/z=394.9. HRMS ($ESI^+$) calculated for $C_{24}H_{21}N_5$: $[M+Na^+]$ m/z=416.1846, found m/z=416.1857.

2-amino-4-(3'-methyl-[1,1'-biphenyl]-3-yl)-6-(piperidin-1-yl)pyridine-3,5-dicarbonitrile (8) (Wherein $R_1$ is 3-Methylphenyl, $R_2$ is a Hydrogen, $R_3$ is Cyano and $R_4$ is Piperidine)

(8)

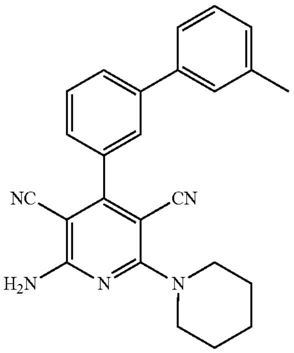

The product was prepared as described above by thermal activation starting from 2-amino-4-(3-bromophenyl)-6-(piperidin-1-yl)pyridine-3,5-dicarbonitrile (intermediate of formula (iiiaa)) (60 mg, 0.16 mmol, 1 eq.) and 3-methylphenylboronic acid (intermediate of formula (iv) wherein $R_1$ is 3-methylphenyl and $R_2$ is boronic acid) (63 mg, 3 eq.) and was isolated as a white powder (47 mg, 0.12 mmol, 76% isolated yield). $^1$H NMR (600 MHz, $CDCl_3$) δ 7.70 (ddd, J=7.7, 1.9, 1.2 Hz, 1H), 7.69 (t, J=1.8 Hz, 1H), 7.57 (t, J=7.7 Hz, 1H), 7.47-7.46 (m, 1H), 7.43 (d, J=8.2 Hz, 1H), 7.34 (t, J=7.9 Hz, 1H), 7.18 (d, J=7.2 Hz, OH), 5.36 (s, 2H), 3.82 (dd, J=5.9, 3.1 Hz, 4H), 2.43 (s, 3H), 1.72 (q, J=1.5 Hz, 4H). $^{13}$C NMR (151 MHz, $CDCl_3$) δ 162.4, 161.4, 159.6, 142.2, 140.6, 138.5, 135.2, 129.3, 128.9, 128.5, 128.3, 127.9, 127.5, 124.7, 117.9, 116.8, 83.8, 81.9, 49.4, 26.2, 24.6, 21.7. MS ($ESI^+$) calculated for $C_{24}H_{21}N_5$: $[M+H^+]$ m/z=394.2, found m/z=394.9. HRMS ($ESI^+$) calculated for $C_{24}H_{21}N_5$: $[M+Na^+]$ m/z=416.1846, found m/z=416.1857.

2-amino-4-(4'-methyl-[1,1'-biphenyl]-3-yl)-6-(piperidin-1-yl)pyridine-3,5-dicarbonitrile (9) (Wherein $R_1$ is 4-Methylphenyl, $R_2$ is a Hydrogen, $R_3$ is Cyano and $R_4$ is Piperdine)

(9)

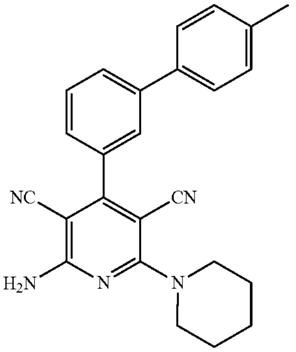

The product was prepared following Sarkar et al., 2014, supra starting from 4'-methyl-[1,1'-biphenyl]-3-carbaldehyde (intermediate of formula (via)) (98 mg, 0.5 mmol, 1 eq.) and was isolated as a white powder (56 mg, 0.14 mmol, 28% isolated yield). $^1$H NMR (600 MHz, $CDCl_3$) δ 7.71-7.67 (m, 2H), 7.56 (t, J=7.6 Hz, 1H), 7.53 (d, J=7.9 Hz, 2H), 7.45 (dd, J=7.7, 1.5 Hz, 1H), 7.26 (d, J=8.1 Hz, 2H), 5.37 (s, 2H), 3.84-3.79 (m, 4H), 1.74-1.69 (m, 6H). $^{13}$C NMR (151 MHz, $CDCl_3$) δ 162.4, 161.4, 159.6, 141.9, 137.8, 137.6, 135.2, 129.7, 129.31, 129.28, 127.7, 127.40, 127.36, 117.9, 116.8, 83.8, 81.8, 49.4, 26.2, 24.6, 21.3. MS ($ESI^+$) calculated for $C_{24}H_{21}N_5$: $[M+H^+]$ m/z=394.2, found m/z=394.8. HRMS ($ESI^+$) calculated for $C_{24}H_{21}N_5$: $[M+Na^+]$ m/z=416.1846, found m/z=416.1857.

2-amino-6-(piperidin-1-yl)-4-(3-(pyridin-2-yl)phenyl)pyridine-3,5-dicarbonitrile (10) (Wherein $R_1$ is 2-Pyridinyl, $R_2$ is a Hydrogen, $R_3$ is Cyano and $R_4$ is Piperidine)

(10)

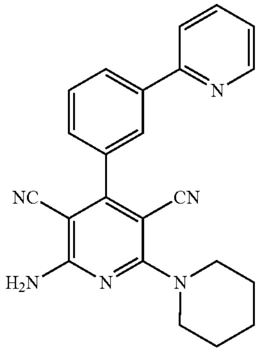

The product was prepared as described above using microwave-assisted Suzuki cross-coupling at 80° C. for 15 min, starting from (3-(2-amino-3,5-dicyano-6-(piperidin-1-yl)pyridin-4-yl)phenyl)boronic acid pinacol ester (intermediate of formula (iiiba)) (64 mg, 0.15 mmol, 1 eq.) and 2-bromopyridine (intermediate of formula (iv) wherein $R_1$ is 2-pyridinyl and $R_2$ is bromo) (28 mg, 1.2 eq.) and was isolated as a white powder (17 mg, 0.04 mmol, 30% isolated yield). $^1$H NMR (600 MHz, $CDCl_3$) δ 8.92 (s, 1H), 8.65 (s, 1H), 7.99 (dt, J=8.0, 1.8 Hz, 1H), 7.75-7.68 (m, 2H), 7.64 (t, J=7.7 Hz, 1H), 7.56 (dt, J=7.7, 1.4 Hz, 1H), 7.44 (t, J=5.9 Hz, 1H), 5.40 (s, 2H), 3.86-3.80 (m, 4H), 1.76-1.70 (m, 6H). $^{13}$C NMR (151 MHz, $CDCl_3$) δ 162.0, 161.1, 159.4, 135.4, 129.39, 129.36, 129.0, 127.5, 122.7, 121.1, 117.6, 116.5, 83.7, 81.7, 49.2, 26.0, 24.4. MS ($ESI^+$) calculated for $C_{23}H_{20}N_6$: $[M+H^+]$ m/z=381.2, found m/z=381.0. HRMS ($ESI^+$) calculated for $C_{23}H_{20}N_6$: $[M+H^+]$ m/z=381.1823, found m/z=381.1803.

2-amino-6-(piperidin-1-yl)-4-(3-(pyridin-3-yl)phenyl)pyridine-3,5-dicarbonitrile (11) (Wherein $R_1$ is 3-Pyridinyl, $R_2$ is a Hydrogen, $R_3$ is Cyano and $R_4$ is Piperidine)

(11)

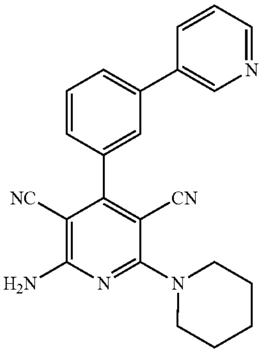

The product was prepared as described above using microwave-assisted Suzuki cross-coupling at 100° C. for 30 min, starting from 2-amino-4-(3-bromophenyl)-6-(piperidin-1-yl)pyridine-3,5-dicarbonitrile (intermediate of formula (iiiaa)) (58 mg, 0.15 mmol, 1 eq.) and 3-pyridineboronic acid (intermediate of formula (iv) wherein $R_1$ is 3-pyridinyl and $R_2$ is boronic acid) (55 mg, 3 eq.) and was isolated as a white powder (79 mg, 0.15 mmol, quantitative isolated yield). $^1H$ NMR (600 MHz, $CDCl_3$) δ 8.92 (s, 1H), 8.65 (s, 1H), 7.99 (dt, J=8.0, 1.8 Hz, 1H), 7.75-7.68 (m, 2H), 7.64 (t, J=7.7 Hz, 1H), 7.56 (dt, J=7.7, 1.4 Hz, 1H), 7.44 (t, J=5.9 Hz, 1H), 5.40 (s, 2H), 3.86-3.80 (m, 4H), 1.76-1.70 (m, 6H). $^{13}C$ NMR (151 MHz, $CDCl_3$) δ 161.9, 161.2, 159.6, 149.1, 148.6, 138.7, 136.1, 135.7, 134.9, 129.8, 129.4, 128.5, 127.9, 123.8, 117.9, 116.7, 83.6, 81.8, 49.4, 26.2, 24.6. MS ($ESI^+$) calculated for $C_{23}H_{20}N_6$: $[M+H^+]$ m/z=381.2, found m/z=381.1. HRMS ($ESI^+$) calculated for $C_{23}H_{20}N_6$: $[M+H^+]$ m/z=381.1823, found m/z=381.1836.

2-amino-6-(piperidin-1-yl)-4-(3-(pyridin-4-yl)phenyl)pyridine-3,5-dicarbonitrile (12) (Wherein $R_1$ is 4-Pyridinyl, $R_2$ is a Hydrogen, $R_3$ is Cyano and $R_4$ is Piperidine)

(12)

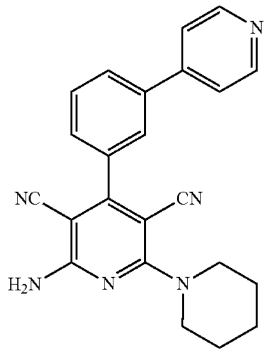

The product was prepared as described above using microwave-assisted Suzuki cross-coupling at 80° C. for 15 min, starting from 2-amino-4-(3-bromophenyl)-6-(piperidin-1-yl)pyridine-3,5-dicarbonitrile (intermediate of formula (iiiaa)) (58 mg, 0.15 mmol, 1 eq.) and 4-pyridineboronic acid (intermediate of formula (iv) wherein $R_1$ is 4-pyridinyl and $R_2$ is boronic acid) (55 mg, 3 eq.) and was isolated as a white powder (5 mg, 0.013 mmol, 9% isolated yield). $^1H$ NMR (600 MHz, $CDCl_3$) δ 8.71-8.67 (m, 2H), 7.79-7.74 (m, 2H), 7.65 (t, J=8.1 Hz, 1H), 7.61-7.58 (m, 3H), 5.41 (s, 2H), 3.86-3.80 (m, 4H), 1.75-1.69 (m, 7H). $^{13}C$ NMR (151 MHz, $CDCl_3$) δ 161.7, 161.2, 159.6, 149.3, 138.6, 136.0, 132.4, 132.3, 130.1, 129.4, 128.8, 128.7, 128.1, 122.6, 117.9, 116.8, 83.6, 81.8, 49.5, 26.3, 24.6. MS ($ESI^+$) calculated for $C_{23}H_{20}N_6$: $[M+H^+]$ m/z=381.2, found m/z=381.1. HRMS ($ESI^+$) calculated for $C_{23}H_{20}N_6$: $[M+H^+]$ m/z=381.1823, found m/z=381.1836.

2-amino-6-(piperidin-1-yl)-4-(3-(thiophen-2-yl)phenyl)pyridine-3,5-dicarbonitrile (13) (Wherein $R_1$ is 2-Thiophenyl, $R_2$ is a Hydrogen, $R_3$ is Cyano and $R_4$ is Piperidine)

(13)

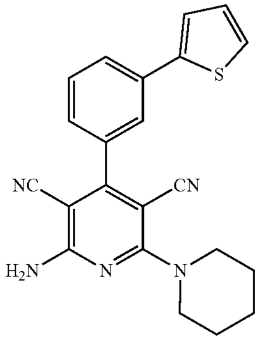

The product was prepared as described above using microwave-assisted Suzuki cross-coupling at 100° C. for 30 min, starting from 2-amino-4-(3-bromophenyl)-6-(piperidin-1-yl)pyridine-3,5-dicarbonitrile (intermediate of formula (iiiaa)) (58 mg, 0.16 mmol, 1 eq.) and 2-thiopheneboronic acid (intermediate of formula (iv) wherein $R_1$ is 2-thiophenyl and $R_2$ is boronic acid) (23 mg, 3 eq.) and was isolated as a white powder (58 mg, 0.16 mmol, quantitative isolated yield). $^1H$ NMR (600 MHz, $CDCl_3$) δ 7.74 (ddd, J=7.8, 1.9, 1.1 Hz, 1H), 7.71 (t, J=1.8 Hz, 1H), 7.52 (t, J=7.8 Hz, 1H), 7.39 (ddd, J=7.7, 1.8, 1.1 Hz, 1H), 7.37 (dd, J=3.6, 1.2 Hz, 1H), 7.31 (dd, J=5.1, 1.2 Hz, 1H), 7.09 (dd, J=5.1, 3.6 Hz, 1H), 5.44 (s, 2H), 3.85-3.80 (m, 4H), 1.75-1.69 (m, 6H). $^{13}C$ NMR (151 MHz, $CDCl_3$) δ 162.0, 161.0, 159.4, 143.4, 135.5, 135.2, 129.6, 128.25, 128.16, 127.7, 126.3, 125.6, 124.1, 117.6, 116.5, 83.8, 81.9, 49.5, 26.2, 24.5. MS ($ESI^+$) calculated for $C_{22}H_{19}N_5S$: $[M+H^+]$ m/z=386.1, found m/z=386.1. HRMS ($ESI^+$) calculated for $C_{22}H_{19}N_5S$: $[M+H^+]$ m/z=386.1435, found m/z=386.1438.

2-amino-6-(piperidin-1-yl)-4-(3-(thiophen-3-yl)phenyl)pyridine-3,5-dicarbonitrile (14) (Wherein $R_1$ is 3-Thiophenyl, $R_2$ is a Hydrogen, $R_3$ is Cyano and $R_4$ is Piperidine)

(14)

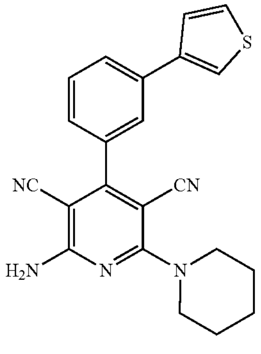

The product was prepared as described above using microwave-assisted Suzuki cross-coupling at 80° C. for 15 min, starting from 2-amino-4-(3-bromophenyl)-6-(piperidin-1-yl)pyridine-3,5-dicarbonitrile (intermediate of formula (iiiaa)) (58 mg, 0.16 mmol, 1 eq.) and 3-thiopheneboronic acid (intermediate of formula (iv) wherein $R_1$ is 3-thiophenyl and $R_2$ is boronic acid) (23 mg, 1.2 eq.) and was isolated as a white powder (42 mg, 0.11 mmol, 73% isolated yield). $^1H$ NMR (600 MHz, $CDCl_3$) δ 7.66-7.62 (m, 2H), 7.46 (t, J=7.7 Hz, 1H), 7.44 (dd, J=2.9, 1.4 Hz, 1H), 7.36-7.33 (m, 2H), 7.32 (dd, J=5.0, 2.9 Hz, 1H), 5.33 (s, 2H), 3.76-3.72 (m, 4H), 1.69-1.62 (m, 6H). $^{13}C$ NMR (151 MHz, $CDCl_3$) δ 162.2, 161.3, 159.6, 141.7, 136.6, 135.4, 129.4, 128.7, 127.5, 127.1, 126.59, 126.55, 121.4, 117.8, 116.7, 83.7, 81.8, 49.4, 26.1, 24.6. MS ($ESI^+$) calculated for $C_{22}H_{19}N_5S$: [$M+Na^+$] m/z=408.1, found m/z=408.0. HRMS ($ESI^+$) calculated for $C_{22}H_{19}N_5S$: [$M+H^+$] m/z=386.1435, found m/z=386.1438.

4-(3-(1H-pyrazol-5-yl)phenyl)-2-amino-6-(piperidin-1-yl)pyridine-3,5-dicarbonitrile (15) (Wherein $R_1$ is 1H-Pyrazol-5-Yl, $R_2$ is a Hydrogen, $R_3$ is Cyano and $R_4$ is Piperidine)

(15)

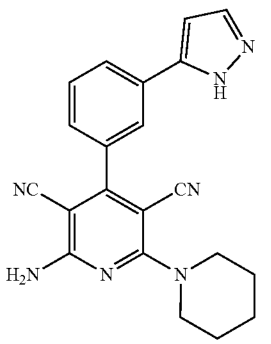

A Suzuki cross-coupling step was performed using microwave-assisted Suzuki cross-coupling starting from (3-(2-amino-3,5-dicyano-6-(piperidin-1-yl)pyridin-4-yl)phenyl) boronic acid pinacol ester (intermediate of formula (iiiba)) (64 mg, 0.15 mmol, 1 eq.) and 5-bromo-1-(tetrahydro-2H-pyran-2-yl)-1H-pyrazole (intermediate of formula (iva)) (42 mg, 1.2 eq.). The deprotection of the pyrazole was done in a dry 10 mL round-bottom flask flushed with argon. The intermediate (1 eq.) was solubilized in a 1:1 DCM:MeOH mix (3 mL). TsOH (39 mg, 1.5 eq.) was added and the solution was stirred at r.t. for 20 h. Completion was assessed by TLC (Rf=0.18 in MixA). Two purifications were performed by flash chromatography on a pre-packed 4 g silica cartridge with a MixA[3]:MeOH isocratic gradient (9:1, 12 CV) then a cyclo:DCM gradient (95:5, 3 CV; 95:5→0:10, 18 CV; methanol wash) (42 mg, 0.11 mmol, 76% global isolated yield). $^1H$ NMR (600 MHz, $CDCl_3$) δ 7.88 (dt, J=7.8, 1.4 Hz, 1H), 7.86 (t, J=1.8 Hz, 1H), 7.63 (s, 1H), 7.53 (t, J=7.7 Hz, 1H), 7.44 (dt, J=7.8, 1.3 Hz, 1H), 6.65 (s, 1H), 5.33 (s, 2H), 3.77-3.73 (m, 4H), 1.67-1.62 (m, 6H). $^{13}C$ NMR (151 MHz, $CDCl_3$) δ 161.8, 161.1, 159.5, 135.8, 129.7, 129.2, 128.3, 126.7, 117.7, 116.6, 83.7, 81.8, 49.4, 26.2, 24.6. MS ($ESI^+$) calculated for $C_{21}H_{19}N_7$: [$M+H^+$] m/z=370.2, found m/z=370.3. HRMS ($ESI^+$) calculated for $C_{21}H_{19}N_7$: [$M+H^+$] m/z=370.1775, found m/z=370.1779.

4-(3-(1H-tetrazol-5-yl)phenyl)-2-amino-6-(piperidin-1-yl)pyridine-3,5-dicarbonitrile (16) (Wherein $R_1$ is 1H-Tetrazol-5-Yl, $R_2$ is a Hydrogen, $R_3$ is Cyano and $R_4$ is Piperidine)

(16)

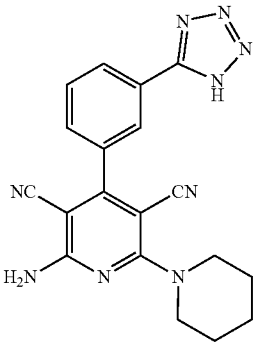

The product was prepared following the genera procedure under Scheme 4 starting from 3-(2-(tetrahydro-2H-pyran-2-yl)-2H-tetrazol-5-yl)benzaldehyde (intermediate of formula (vie)) (60 mg, 0.23 mmol, 1 eq.) and purified by flash chromatography on a pre-packed 4 g silica cartridge with a cyclo:DCM gradient (95:5, 3 CV; 95:5→0:10, 18 CV; methanol wash). The deprotection of the tetrazole was performed in the presence of Dowex 50WX8 $H^+$ (1 g of resin for 100 mg of compound), in a 98:2 EtOH:$H_2O$ mix (1 mL) at 80° C. for 16 h. The resin was filtered off and rinsed with warm EtOH (3x2 mL) and the product was isolated as a white powder (10 mg, 0.03 mmol, 11% global isolated yield). $^1H$ NMR (600 MHz, $(CD_3)_2SO$) δ 10.20 (s, 1H), 8.20 (dt, J=7.8, 1.5 Hz, 1H), 8.15 (t, J=1.8 Hz, 1H), 7.78 (t, J=7.7 Hz, 1H), 7.72 (d, J=7.7 Hz, 1H), 7.50 (s, 2H), 3.77-3.73 (m, 4H), 1.68-1.58 (m, 6H). MS ($ESI^-$) calculated for $C_{19}H_{17}N_9$: [$M-H^+$] m/z=370.2, found m/z=370.0. HRMS ($ESI^-$) calculated for $C_{19}H_{17}N_9$: [$M-H^+$] m/z=370.1524, found m/z=370.1500.

4-([1,1'-biphenyl]-3-yl)-2-amino-6-(diethylamino) pyridine-3,5-dicarbonitrile (17) (Wherein $R_1$ is Phenyl, $R_2$ is a Hydrogen, $R_3$ is Cyano and $R_4$ is Diethylamino)

(17)

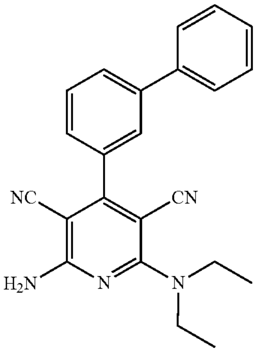

The product was prepared following the general procedure under Scheme 1 starting from 4-([1,1'-biphenyl]-3-yl)-

2-amino-6-chloropyridine-3,5-dicarbonitrile (50 mg, 0.15 mmol) (intermediate of formula (i) wherein $R_1$ is phenyl, $R_2$ is a hydrogen and $R_3$ is a cyano) and diethylamine (0.10 mL, 6 eq.) (nucleophile of formula (ii)) and was isolated as a white amorphous powder (22 mg, 0.06 mmol, 40% isolated yield). $^1H$ NMR (600 MHz, $CDCl_3$) δ 7.71 (dt, J=7.8, 1.4 Hz, 1H), 7.68 (t, J=1.8 Hz, 1H), 7.66-7.61 (m, 2H), 7.58 (t, J=7.7 Hz, 1H), 7.48-7.42 (m, 3H), 7.36 (dd, J=7.4, 1.4 Hz, 1H), 5.50 (s, 2H), 3.77 (q, J=7.0 Hz, 4H), 1.32 (t, J=7.0 Hz, 6H). $^{13}C$ NMR (151 MHz, $CDCl_3$) δ 162.9, 159.0, 158.5, 141.9, 140.7, 135.5, 129.34, 129.32, 129.0, 127.8, 127.6, 127.5, 118.1, 116.7, 81.8, 81.6, 45.0, 13.7. MS ($ESI^+$) calculated for $C_{23}H_{21}N_5$: $[M+H^+]$ m/z=368.2, found m/z=368.4. HRMS ($ESI^+$) calculated for $C_{23}H_{21}N_5$: $[M+H^+]$ m/z=368.1870, found m/z=368.1839.

4-([1,1'-biphenyl]-3-yl)-2-amino-6-morpholinopyridine-3,5-dicarbonitrile (18) (Wherein $R_1$ is Phenyl, $R_2$ is a Hydrogen, $R_3$ is Cyano and $R_4$ is Morpholine)

(18)

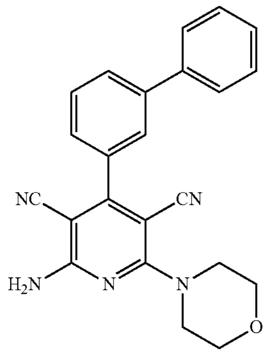

The product was prepared following the general procedure under Scheme 1 starting from 4-([1,1'-biphenyl]-3-yl)-2-amino-6-chloropyridine-3,5-dicarbonitrile (50 mg, 0.15 mmol) (intermediate of formula (i) wherein $R_1$ is phenyl, $R_2$ is a hydrogen and $R_3$ is a cyano) and morpholine (0.10 mL, 8 eq.) (nucleophile of formula (ii)) and was isolated as a white amorphous powder (12 mg, 0.03 mmol, 21% isolated yield). $^1H$ NMR (600 MHz, $CDCl_3$) δ 7.73 (dt, J=7.8, 1.4 Hz, 1H), 7.70 (t, J=1.8 Hz, 1H), 7.65-7.61 (m, 2H), 7.59 (t, J=7.7 Hz, 1H), 7.50-7.43 (m, 3H), 7.37 (dd, J=7.4, 1.2 Hz, 1H), 5.51 (s, 2H), 3.88 (dd, J=5.7, 3.6 Hz, 4H), 3.82 (dd, J=5.6, 3.7 Hz, 4H). $^{13}C$ NMR (151 MHz, $CDCl_3$) δ 162.4, 161.5, 159.5, 142.1, 140.5, 134.9, 129.7, 129.5, 129.0, 127.88, 127.85, 127.6, 127.5, 117.5, 116.3, 84.3, 83.0, 66.8, 48.5. MS ($ESI^+$) calculated for $C_{23}H_{19}N_5O$: $[M+H^+]$ m/z=382.2, found m/z=328.3. HRMS ($ESI^+$) calculated for $C_{23}H_{19}N_5O$: $[M+H^+]$ m/z=382.1663, found m/z=328.1636.

4-([1,1'-biphenyl]-3-yl)-2-amino-6-(4-methylpiperazin-1-yl)pyridine-3,5-dicarbonitrile (19) (Wherein $R_1$ is Phenyl, $R_2$ is a Hydrogen, $R_3$ is Cyano and $R_4$ is N-Methylpiperazine)

(19)

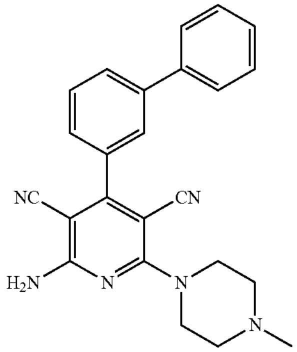

The product was prepared following the general procedure under Scheme 1 starting from 4-([1,1'-biphenyl]-3-yl)-2-amino-6-chloropyridine-3,5-dicarbonitrile (50 mg, 0.15 mmol) (intermediate of formula (i) wherein $R_1$ is phenyl, $R_2$ is a hydrogen and $R_3$ is a cyano) and N-methylpiperazine (0.10 mL, 6 eq.) (nucleophile of formula (ii)) and was isolated as a white amorphous powder (13 mg, 0.03 mmol, 22% isolated yield). $^1H$ NMR (600 MHz, $CD_3OD$) δ 7.79 (ddd, J=7.8, 1.9, 1.1 Hz, 1H), 7.76 (t, J=1.8 Hz, 1H), 7.70-7.65 (m, 2H), 7.62 (t, J=7.7 Hz, 1H), 7.51 (ddd, J=7.7, 1.8, 1.1 Hz, 1H), 7.49-7.43 (m, 2H), 7.38 (dd, J=7.4, 1.1 Hz, 1H), 3.89 (t, J=5.1 Hz, 4H), 2.71 (t, J=4.9 Hz, 4H), 2.45 (s, 3H). $^{13}C$ NMR (151 MHz, $CD_3OD$) δ 163.6, 163.3, 161.9, 143.1, 141.7, 137.0, 130.3, 130.0, 128.8, 128.78, 128.76, 128.3, 118.9, 117.1, 84.2, 83.5, 55.5, 48.2, 45.6. MS ($ESI^+$) calculated for $C_{24}H_{22}N_6$: $[M+H^+]$ m/z=395.2, found m/z=395.5. HRMS ($ESI^+$) calculated for $C_{24}H_{22}N_6$: $[M+H^+]$ m/z=395.1979, found m/z=395.1955.

4-([1,1'-biphenyl]-3-yl)-2-amino-6-(benzylthio)pyridine-3,5-dicarbonitrile (20) (Wherein $R_1$ is Phenyl, $R_2$ is a Hydrogen, $R_3$ is Cyano and $R_4$ is Benzyl Mercaptan)

(20)

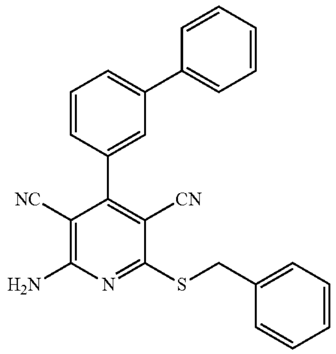

The product was prepared following the general procedure under Scheme 1 starting from 4-([1,1'-biphenyl]-3-yl)-2-amino-6-chloropyridine-3,5-dicarbonitrile (50 mg, 0.15 mmol) (intermediate of formula (i) wherein $R_1$ is phenyl, $R_2$ is a hydrogen and $R_3$ is a cyano), benzylmercaptan (0.03 mL, 1.5 eq.) (nucleophile of formula (ii)) and triethylamine (0.04 mL, 2 eq.) and was isolated as a white amorphous powder (19 mg, 0.04 mmol, 30% isolated yield). $^1H$ NMR (600 MHz, $CDCl_3$) δ 7.75 (dt, J=7.9, 1.4 Hz, 1H), 7.72 (t, J=1.8 Hz, 1H), 7.64-7.58 (m, 3H), 7.50 (dt, J=7.8, 1.3 Hz, 1H), 7.46 (t, J=7.7 Hz, 2H), 7.43-7.40 (m, 2H), 7.40-7.36 (m, 1H), 7.34 (dd, J=8.3, 6.6 Hz, 2H), 7.32-7.27 (m, 1H), 5.70 (s, 2H), 4.48 (s, 2H). $^{13}C$ NMR (151 MHz, $CDCl_3$) δ 168.9, 159.4, 158.2, 142.3, 140.3, 136.2, 133.7, 129.9, 129.7, 129.2, 129.1, 128.9, 127.99, 127.87, 127.65, 127.55, 127.3, 115.6, 114.9, 96.8, 87.0, 35.1. MS ($ESI^-$) calculated for $C_{26}H_{18}N_4S$: $[M-H^+]$ m/z=417.1, found m/z=416.8. HRMS ($ESI^+$) calculated for $C_{26}H_{18}N_4S$: $[M+Na^+]$ m/z=441.1145, found m/z=441.1118.

4-([1,1'-biphenyl]-3-yl)-2-amino-6-methoxypyridine-3,5-dicarbonitrile (21) (Wherein $R_1$ is Phenyl, $R_2$ is a Hydrogen, $R_3$ is Cyano and $R_4$ is Methoxy)

(21)

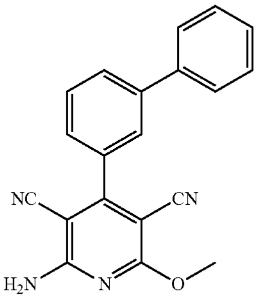

The product was prepared following the general procedure under Scheme 1 starting from 4-([1,1'-biphenyl]-3-yl)-2-amino-6-chloropyridine-3,5-dicarbonitrile (33 mg, 0.10 mmol) (intermediate of formula (i) wherein $R_1$ is phenyl, $R_2$ is a hydrogen and $R_3$ is a cyano), methanol (1 mL) (nucleophile of formula (ii)) and lithium diisopropylamine 1.8 M in THE (0.19 mL, 3 eq.) was isolated as a white amorphous powder (22 mg, 0.07 mmol, 67% isolated yield). 1H NMR (600 MHz, $(CD_3)_2SO$) δ 8.09 (broad s, 2H), 7.89-7.85 (m, 1H), 7.84 (d, J=1.9 Hz, 1H), 7.76-7.71 (m, 2H), 7.67 (t, J=7.7 Hz, 1H), 7.55-7.50 (m, 3H), 7.44-7.40 (m, 1H), 4.00 (s, 3H). $^{13}C$ NMR (151 MHz, $(CD_3)_2SO$) δ 165.8, 161.2, 160.5, 140.4, 139.3, 134.6, 129.4, 129.1, 128.6, 127.9, 127.4, 126.90, 126.87, 115.6, 115.2, 83.4, 83.3, 54.8. MS ($ESI^+$) calculated for $C_{20}H_{14}N_4O$: $[M+Na^+]$ m/z=349.1, found m/z=349.0.

4-([1,1'-biphenyl]-3-yl)-2-amino-6-ethoxypyridine-3,5-dicarbonitrile (22) (Wherein $R_1$ is Phenyl, $R_2$ is a Hydrogen, $R_3$ is Cyano and $R_4$ is Ethoxy)

(22)

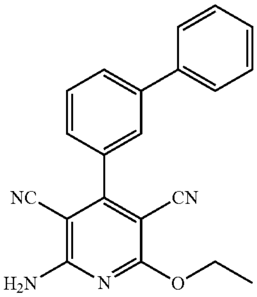

The product was prepared following the general procedure under Scheme 1 starting from 4-([1,1'-biphenyl]-3-yl)-2-amino-6-chloropyridine-3,5-dicarbonitrile (25 mg, 0.07 mmol) (intermediate of formula (i) wherein $R_1$ is phenyl, $R_2$ is a hydrogen and $R_3$ is a cyano), ethanol (1 mL) (nucleophile of formula (ii)) and lithium diisopropylamine 1.8 M in THE (0.13 mL, 3 eq.) was isolated as a white amorphous powder (19 mg, 0.055 mmol, 80% isolated yield). $^1H$ NMR (600 MHz, $(CD_3)_2SO$) δ 7.97 (broad s, 2H), 7.86 (ddd, J=7.8, 1.9, 1.1 Hz, 1H), 7.84 (t, J=1.8 Hz, 1H), 7.75-7.70 (m, 2H), 7.66 (t, J=7.7 Hz, 1H), 7.55-7.48 (m, 3H), 7.45-7.39 (m, 1H), 4.46 (q, J=7.1 Hz, 2H), 1.36 (t, J=7.1 Hz, 3H). $^{13}C$ NMR (151 MHz, $(CD_3)_2SO$) δ 165.4, 161.2, 160.6, 140.4, 139.3, 134.7, 129.4, 129.1, 128.5, 127.9, 127.4, 126.91, 126.87, 115.7, 115.2, 83.5, 83.1, 63.4, 14.3. MS ($ESI^+$) calculated for $C_{21}H_{16}N_{40}$: $[M+Na^+]$ m/z=363.1, found m/z=363.0.

4-([1,1'-biphenyl]-3-yl)-2-amino-6-(2-hydroxyethoxy)pyridine-3,5-dicarbonitrile (23) (Wherein $R_1$ is Phenyl, $R_2$ is a Hydrogen, $R_3$ is Cyano and $R_4$ is Ethoxy, 1-ol)

(23)

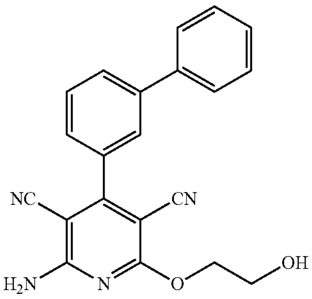

The product was prepared following the general procedure under Scheme 1 starting from 4-([1,1'-biphenyl]-3-yl)-2-amino-6-chloropyridine-3,5-dicarbonitrile (33 mg, 0.10 mmol) (intermediate of formula (i) wherein $R_1$ is phenyl, $R_2$ is a hydrogen and $R_3$ is a cyano), methanol (1 mL) (nucleophile of formula (ii)) and lithium diisopropylamine 1.8 M in THE (0.19 mL, 3 eq.) was isolated as a white amorphous powder (11 mg, 0.03 mmol, 31% isolated yield). $^1H$ NMR (600 MHz, $(CD_3)_2SO$) δ 7.97 (broad s, 2H), 7.87 (dt, J=7.8, 1.5 Hz, 1H), 7.84 (t, J=1.8 Hz, 1H), 7.76-7.72 (m, 2H), 7.66 (t, J=7.7 Hz, 1H), 7.55-7.48 (m, 3H), 7.46-7.39 (m, 1H), 4.91 (t, J=5.3 Hz, 1H), 4.43 (t, J=5.1 Hz, 2H), 3.74 (q, J=5.2 Hz, 2H). $^{13}$C NMR (151 MHz, $(CD_3)_2SO$) δ 165.6, 161.1, 160.6, 140.4, 139.3, 134.7, 129.4, 129.1, 128.6, 127.9, 127.4, 126.90, 126.86, 115.6, 115.2, 83.6, 83.2, 69.0, 58.9. MS ($ESI^+$) calculated for $C_{21}H_{16}N_4O_2$: [$M+Na^+$] m/z=379.1, found m/z=379.0.

2-amino-4-(3-(3-fluoropyridin-2-yl)phenyl)-6-(piperidin-1-yl)pyridine-3,5-dicarbonitrile (24) (Wherein $R_1$ is 3-Fluoro-2-Pyridinyl, $R_2$ is a Hydrogen, $R_3$ is Cyano and $R_4$ is Piperidine)

(24)

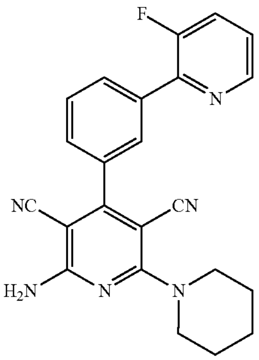

The product was prepared as described above using microwave-assisted Suzuki cross-coupling at 80° C. for 15 min, starting from (3-(2-amino-3,5-dicyano-6-(piperidin-1-yl)pyridin-4-yl)phenyl)boronic acid pinacol ester (intermediate of formula (iiiba)) (100 mg, 0.23 mmol, 1 eq.) and 2-bromo-3-fluoropyridine (intermediate of formula (iv) wherein $R_1$ is 3-fluoro-2-pyridinyl and $R_9$ is bromo) (53 mg, 1.2 eq.) and was isolated as a white powder (66 mg, 0.16 mmol, 72% isolated yield). $^1$H NMR (600 MHz, $CDCl_3$) δ 8.54 (dt, J=4.6, 1.6 Hz, 1H), 8.19 (dd, J=7.8, 1.5 Hz, 1H), 8.17 (d, J=1.5 Hz, 1H), 7.64 (t, J=7.7 Hz, 1H), 7.57 (dt, J=7.7, 1.4 Hz, 1H), 7.53 (ddd, J=11.0, 8.2, 1.4 Hz, 1H), 7.31 (p, J=4.2 Hz, 1H), 5.44 (s, 2H), 3.84-3.79 (m, 4H), 1.73-1.70 (m, 6H). $^{13}$C NMR (151 MHz, $CDCl_3$) δ 162.1, 161.1, 159.5, 157.9 (d, J=261.4 Hz), 145.5 (d, J=5.2 Hz), 145.0 (d, J=10.3 Hz), 135.8 (d, J=5.6 Hz), 135.2, 131.0 (d, J=6.6 Hz), 129.7, 129.3 (d, J=6.1 Hz), 129.2, 124.7 (d, J=20.6 Hz), 124.1 (d, J=4.1 Hz), 117.6, 116.5, 83.9, 82.0, 49.5, 26.2, 24.5. MS ($ESI^+$) calculated for $C_{23}H_{19}N_6F$: [$M+H^+$] m/z=399.2, found m/z=399.1. HRMS ($ESI^+$) calculated for $C_{23}H_{19}N_6F$: [$M+H^+$]m/z=399.1728, found m/z=399.1701.

2-amino-4-(3-(6-fluoropyridin-2-yl)phenyl)-6-(piperidin-1-yl)pyridine-3,5-dicarbonitrile (25) (Wherein $R_1$ is 6-Fluoro-2-Pyridinyl, $R_2$ is a Hydrogen, $R_3$ is Cyano and $R_4$ is Piperidine)

(25)

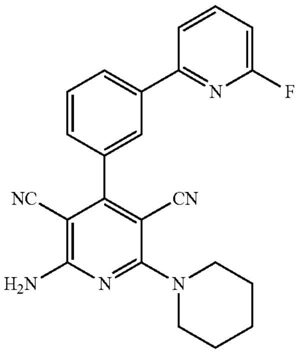

The product was prepared as described above using microwave-assisted Suzuki cross-coupling at 80° C. for 15 min, starting from (3-(2-amino-3,5-dicyano-6-(piperidin-1-yl)pyridin-4-yl)phenyl)boronic acid pinacol ester (intermediate of formula (iiiba)) (100 mg, 0.23 mmol, 1 eq.) and 2-bromo-6-fluoropyridine (intermediate of formula (iv) wherein $R_1$ is 6-fluoro-2-pyridinyl and $R_9$ is bromo) (53 mg, 1.2 eq.) and was isolated as a white powder (35 mg, 0.09 mmol, 38% isolated yield). $^1$H NMR (600 MHz, $CDCl_3$) δ 8.17-8.12 (m, 2H), 7.86 (q, J=8.0 Hz, 1H), 7.68 (dd, J=7.4, 2.2 Hz, 1H), 7.64-7.61 (m, 1H), 7.55 (dt, J=7.6, 1.5 Hz, 1H), 6.90 (dd, J=8.1, 3.0 Hz, 1H), 5.47 (s, 2H), 3.85-3.80 (m, 4H), 1.75-1.69 (m, 6H). $^{13}$C NMR (151 MHz, $CDCl_3$) δ 163.6 (d, J=238.9 Hz), 162.1, 160.9, 159.34, 155.4 (d, J=13.4 Hz), 141.9 (d, J=7.7 Hz), 138.3, 135.5, 129.8, 129.5, 129.0, 127.6, 117.8 (d, J=4.0 Hz), 117.6, 116.5, 108.4 (d, J=37.5 Hz), 83.8, 81.9, 49.5, 26.2, 24.5. MS ($ESI^+$) calculated for $C_{23}H_{19}N_6F$: [$M+H^+$] m/z=399.2, found m/z=399.2. HRMS ($ESI^+$) calculated for $C_{23}H_{19}N_6F$: [$M+H^+$] m/z=399.1728, found m/z=399.1701.

2-amino-4-(3-(4-fluoropyridin-2-yl)phenyl)-6-(piperidin-1-yl)pyridine-3,5-dicarbonitrile (26) (Wherein $R_1$ is 4-Fluoro-2-Pyridinyl, $R_2$ is a Hydrogen, $R_3$ is Cyano and $R_4$ is Piperidine)

(26)

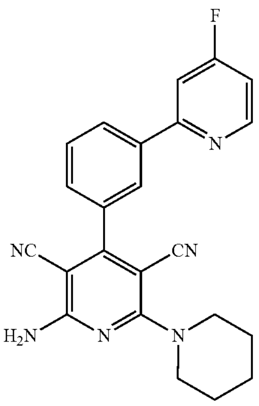

The product was prepared as described above using microwave-assisted Suzuki cross-coupling at 80° C. for 15 min, starting from (3-(2-amino-3,5-dicyano-6-(piperidin-1-yl)pyridin-4-yl)phenyl)boronic acid pinacol ester (intermediate of formula (iiiba)) (100 mg, 0.23 mmol, 1 eq.) and 2-bromo-4-fluoropyridine (intermediate of formula (iv) wherein $R_1$ is 4-fluoro-2-pyridinyl and $R_9$ is bromo) (53 mg, 1.2 eq.) and was isolated as a white powder (35 mg, 0.09 mmol, 38% isolated yield). $^1$H NMR (600 MHz, $CDCl_3$) δ 8.70 (dd, J=8.5, 5.6 Hz, 1H), 8.17 (d, J=7.8 Hz, 1H), 8.14 (s, 1H), 7.66 (t, J=7.7 Hz, 1H), 7.60 (dd, J=7.7, 1.6 Hz, 1H), 7.54 (dd, J=10.1, 2.4 Hz, 1H), 7.05 (ddd, J=6.5, 5.1, 2.6 Hz, 1H), 5.39 (s, 2H), 3.84-3.80 (m, 4H), 1.74-1.70 (m, 6H). $^{13}$C NMR (151 MHz, $CDCl_3$) δ 169.9 (d, J=264.1 Hz), 161.8, 161.1, 159.5, 151.7, 135.7, 130.3, 129.7, 129.2, 127.8, 117.7, 116.6, 110.8 (d, J=17.0 Hz), 109.0 (d, J=17.8 Hz), 83.7, 81.8, 49.4, 26.2, 24.6. MS (ESI*) calculated for $C_{23}H_{19}N_6F$: [M+H$^+$] m/z=399.2, found m/z=399.2. HRMS (ESI$^+$) calculated for $C_{23}H_{19}N_6F$: [M+H$^+$]m/z=399.1728, found m/z=399.1701.

2-amino-4-(3-(5-fluoropyridin-3-yl)phenyl)-6-(piperidin-1-yl)pyridine-3,5-dicarbonitrile (27) (Wherein $R_1$ is 5-Fluoro-3-Pyridinyl, $R_2$ is a Hydrogen, $R_3$ is Cyano and $R_4$ is Piperidine)

(27)

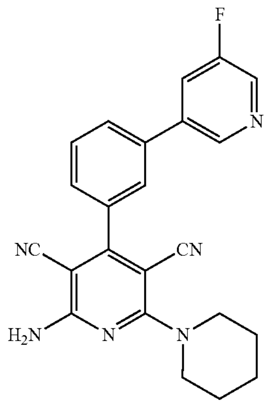

The product was prepared as described above using microwave-assisted Suzuki cross-coupling at 80° C. for 15 min, starting from (3-(2-amino-3,5-dicyano-6-(piperidin-1-yl)pyridin-4-yl)phenyl)boronic acid pinacol ester (intermediate of formula (iiiba)) (100 mg, 0.23 mmol, 1 eq.) and 3-bromo-5-fluoropyridine (intermediate of formula (iv) wherein $R_1$ is 5-fluoro-3-pyridinyl and $R_9$ is bromo) (53 mg, 1.2 eq.) and was isolated as a white powder (76 mg, 0.19 mmol, 83% isolated yield). $^1$H NMR (600 MHz, $CDCl_3$) δ 8.74 (d, J=1.7 Hz, 1H), 8.51 (d, J=2.2 Hz, 1H), 7.72 (ddt, J=19.1, 9.9, 1.6 Hz, 3H), 7.66 (t, J=7.3 Hz, 1H), 7.60 (dd, J=7.7, 1.5 Hz, 1H), 5.43 (s, 2H), 3.85-3.78 (m, 4H), 1.74-1.70 (m, 6H). $^{13}$C NMR (151 MHz, $CDCl_3$) δ 161.5, 161.0, 160.8, 159.5, 143.4, 138.3, 136.7, 136.2, 136.1, 130.1, 129.5, 129.4, 128.0, 122.8, 117.7, 116.6, 83.5, 81.7, 49.4, 26.2, 24.5. MS (ESI$^+$) calculated for $C_{23}H_{19}N_6F$: [M+H$^+$] m/z=399.2, found m/z=399.2. HRMS (ESI$^+$) calculated for $C_{23}H_{19}N_6F$: [M+H$^+$]m/z=399.1728, found m/z=399.1701.

2-amino-4-(3-(2-fluoropyridin-3-yl)phenyl)-6-(piperidin-1-yl)pyridine-3,5-dicarbonitrile (28) (Wherein $R_1$ is 2-Fluoro-3-Pyridinyl, $R_2$ is a Hydrogen, $R_3$ is Cyano and $R_4$ is Piperidine)

(28)

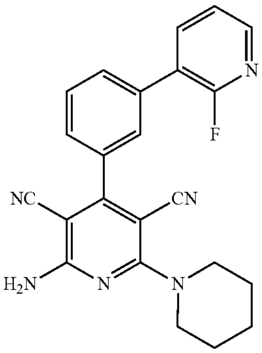

The product was prepared as described above using microwave-assisted Suzuki cross-coupling at 100° C. for 30 min, starting from 2-amino-4-(3-bromophenyl)-6-(piperidin-1-yl)pyridine-3,5-dicarbonitrile (intermediate of formula (iiiaa)) (100 mg, 0.23 mmol, 1 eq.) and 2-fluoro-3-pyridineboronic acid (intermediate of formula (iv) wherein $R_1$ is 2-fluoro-3-pyridinyl and $R_9$ is boronic acid) (109 mg, 3 eq.) and was isolated as a white powder (12 mg, 0.03 mmol, 12% isolated yield). 1H NMR (600 MHz, $(CD_3)_2SO$) δ 8.29 (d, J=4.6 Hz, OH), 8.16 (ddd, J=10.3, 7.4, 1.9 Hz, 1H), 7.81 (dq, J=7.7, 1.6 Hz, 1H), 7.78 (s, 1H), 7.68 (t, J=7.7 Hz, 1H), 7.60 (dt, J=7.7, 1.4 Hz, 1H), 7.52 (ddd, J=6.9, 4.8, 1.7 Hz, 1H), 7.46 (s, 3H), 3.76-3.71 (m, 4H), 1.71-1.55 (m, 6H). 13C NMR (151 MHz, $(CD_3)$ 2SO) δ 161.1, 160.7, 159.8, 159.6 (d, J=237.7 Hz), 146.9 (d, J=14.6 Hz), 141.6 (d, J=4.2 Hz), 135.8, 133.6 (d, J=5.1 Hz), 130.4 (d, J=3.1 Hz), 129.1, 129.0 (d, J=24.0 Hz), 122.8 (d, J=4.2 Hz), 122.2 (d, J=28.2 Hz), 117.8, 116.3, 81.5, 80.8, 48.5, 25.6, 23.9. MS (ESI$^+$) calculated for $C_{23}H_{19}N_6F$: [M+H] m/z=399.2, found m/z=399.5. HRMS (ESI$^+$) calculated for $C_{23}H_{19}N_6F$: [M+H] m/z=399.1728, found m/z=399.1707.

2-amino-4-(2-fluoro-5-(pyridin-3-yl)phenyl)-6-(piperidin-1-yl)pyridine-3,5-dicarbonitrile (29) (Wherein $R_1$ is Pyridinyl, $R_2$ is a 6-Fluoro, $R_3$ is Cyano and $R_4$ is Piperidine)

(29)

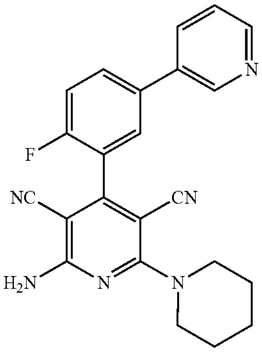

The product was prepared as described above using microwave-assisted Suzuki cross-coupling at 100° C. for 30 min, starting from 2-amino-4-(5-bromo-2-fluorophenyl)-6-(piperidin-1-yl)pyridine-3,5-dicarbonitrile (intermediate of formula (iiiab)) (58 mg, 0.15 mmol, 1 eq.) and 3-pyridine-boronic acid (intermediate of formula (iv) wherein $R_1$ is 3-pyridinyl and $R_9$ is boronic acid) (55 mg, 3 eq.) and was isolated as a white powder (53 mg, 0.13 mmol, 89% isolated yield). $^1$H NMR (600 MHz, $CDCl_3$) δ 8.89 (d, J=2.3 Hz, 1H), 8.66 (dd, J=5.1, 1.5 Hz, 1H), 8.09 (dd, J=8.0, 1.9 Hz, 1H), 7.71 (ddd, J=8.6, 4.6, 2.4 Hz, 1H), 7.61 (dd, J=6.5, 2.4 Hz, 1H), 7.57 (dd, J=8.0, 5.0 Hz, 1H), 7.39 (t, J=8.9 Hz, 1H), 5.41 (s, 2H), 3.86-3.81 (m, 4H), 1.76-1.67 (m, 6H). $^{13}$C NMR (151 MHz, $CDCl_3$) δ 160.4, 159.6 (d, J=253.6 Hz), 159.3, 155.8, 145.9 (d, J=82.0 Hz), 137.3, 136.5, 133.3, 131.3 (d, J=8.4 Hz), 129.8 (d, J=3.1 Hz), 124.8, 124.0 (d, J=15.7 Hz), 117.8 (d, J=22.5 Hz), 117.2, 116.1, 84.3, 82.4, 49.2, 26.2, 24.5. MS ($ESI^+$) calculated for $C_{23}H_{19}N_6F$: $[M+H^+]$ m/z=399.2, found m/z=399.4. HRMS ($ESI^+$) calculated for $C_{23}H_{19}N_6F$: $[M+H^+]$ m/z=399.1728, found m/z=399.1701.

2-amino-4-(2-fluoro-3-(pyridin-3-yl)phenyl)-6-(piperidin-1-yl)pyridine-3,5-dicarbonitrile (30) (Wherein $R_1$ is Pyridinyl, $R_2$ is a 2-Fluoro, $R_3$ is Cyano and $R_4$ is Piperidine)

(30)

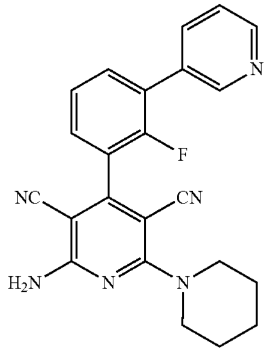

The product was prepared as described above using microwave-assisted Suzuki cross-coupling at 100° C. for 30 min, starting from 2-amino-4-(3-bromo-2-fluorophenyl)-6-(piperidin-1-yl)pyridine-3,5-dicarbonitrile (intermediate of formula (iiiac)) (58 mg, 0.15 mmol, 1 eq.) and 3-pyridine-boronic acid (intermediate of formula (iv) wherein $R_1$ is 3-pyridinyl and $R_9$ is boronic acid) (55 mg, 3 eq.) and was isolated as a paste (15 mg, 0.04 mmol, 25% isolated yield). 1H NMR (600 MHz, $CDCl_3$) δ 8.96-8.94 (m, 1H), 8.77-8.73 (m, 1H), 8.41 (d, J=8.0 Hz, 1H), 7.83 (dd, J=8.0, 5.3 Hz, 1H), 7.63 (td, J=7.4, 1.8 Hz, 1H), 7.55 (ddd, J=8.0, 6.4, 1.7 Hz, 1H), 7.49 (t, J=7.7 Hz, 1H), 5.43 (s, 2H), 3.86-3.80 (m, 4H), 1.77-1.68 (m, 6H). $^{13}$C NMR (151 MHz, $CDCl_3$) δ 160.1, 159.1, 156.1 (d, J=253.4 Hz), 155.6, 143.5, 142.6, 133.9, 132.41 (d, J=2.6 Hz), 132.37, 125.8 (d, J=4.7 Hz), 125.7, 124.4, 124.3, 117.1, 115.9, 84.1, 82.1, 49.1, 26.0, 24.4. MS ($ESI^+$) calculated for $C_{23}H_{19}N_6F$: $[M+H^+]$ m/z=399.2, found m/z=399.4. HRMS ($ESI^+$) calculated for $C_{23}H_{19}N_6F$: $[M+H^+]$ m/z=399.1728, found m/z=399.1701.

2-amino-4-(3-fluoro-5-(pyridin-3-yl)phenyl)-6-(piperidin-1-yl)pyridine-3,5-dicarbonitrile (31) (Wherein $R_1$ is Pyridinyl, $R_2$ is a 5-Fluoro, $R_3$ is Cyano and $R_4$ is Piperidine)

(31)

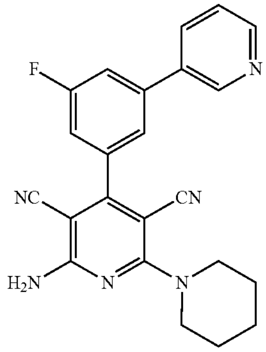

The product was prepared as described above using microwave-assisted Suzuki cross-coupling at 100° C. for 30 min, starting from 2-amino-4-(3-chloro-5-fluorophenyl)-6-(piperidin-1-yl)pyridine-3,5-dicarbonitrile (intermediate of formula (iiiad)) (53 mg, 0.15 mmol, 1 eq.) and 3-pyridine-boronic acid (intermediate of formula (iv) wherein $R_1$ is 3-pyridinyl and $R_9$ is boronic acid) (55 mg, 3 eq.) and was isolated as a white powder (56 mg, 0.14 mmol, 96% isolated yield). $^1$H NMR (600 MHz, $CDCl_3$) δ 8.93 (s, 1H), 8.70 (s, 1H), 8.15 (dt, J=8.0, 1.8 Hz, 1H), 7.65-7.59 (m, 1H), 7.49 (d, J=1.6 Hz, 1H), 7.44 (dt, J=8.9, 1.9 Hz, 1H), 7.31 (dt, J=8.5, 1.9 Hz, 1H), 5.45 (s, 2H), 3.86-3.81 (m, 4H), 1.76-1.68 (m, 6H). $^{13}$C NMR (151 MHz, $CDCl_3$) δ 163.2 (d, J=250.3 Hz), 160.8, 160.1, 159.4, 146.3, 145.4, 138.0 (d, J=8.4 Hz), 137.8, 125.1, 123.8 (d, J=3.1 Hz), 117.5, 116.7 (d, J=23.0 Hz), 116.32 (d, J=22.5 Hz), 116.27, 83.2, 81.5, 49.3, 26.2, 24.5. MS ($ESI^+$) calculated for $C_{23}H_{19}N_6F$: $[M+H^+]$ m/z=399.2, found m/z=399.3. HRMS ($ESI^+$) calculated for $C_{23}H_{19}N_6F$: $[M+H^+]$ m/z=399.1728, found m/z=399.1707.

4-(3-(1,3,4-oxadiazol-2-yl)phenyl)-2-amino-6-(piperidin-1-yl)pyridine-3,5-dicarbonitrile (32) (Wherein $R_1$ is 1,3,4-Oxadiazol, $R_2$ is a Hydrogen, $R_3$ is Cyano and $R_4$ is Piperidine)

(32)

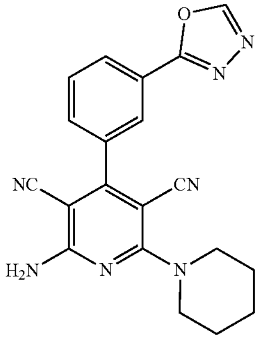

In a 25 mL round-bottom flask equipped with a magnetic stirrer and a condenser, methyl 3-(2-amino-3,5-dicyano-6-

(piperidin-1-yl)pyridin-4-yl)benzoate (54 mg, 0.15 mmol, 1 eq.) was suspended in anhydrous methanol (1.5 mL). Hydrazine monohydrate (37 mg, 5 eq.) was added to the solution then the vessel was purged with argon and sealed. The reaction was heated at 80° C. for 16 h. Solvents were removed under reduced pressure and the crude product was rinsed with DCM:MeOH 7:3 (10 mL) and dried under reduced pressure. In a 25 mL round-bottom flask equipped with a magnetic stirrer and a condenser, the intermediate was suspended in an excess of triethyl orthoformate (1 mL). The vessel was flushed with argon and heated at 100° C. for 20 h. The reaction was quenched by addition of water (20 mL) and the crude product was extracted by EtOAc (3×15 mL). The organic phases were combined, washed with brine, dried over $MgSO_4$ and the solvent was removed under reduced pressure. The crude product was purified by flash chromatography on a silica cartridge on 12 g silica cartridge, solid deposit, with a cyclo:EtOAc gradient (8:2, 3 CV; 8:2→6:4, 12 CV; 6:4, 6 CV) and isolated as a white powder (32 mg, 0.09 mmol, 58% overall isolated yield). $^1H$ NMR (600 MHz, $CDCl_3$) δ 8.50 (s, 1H), 8.26 (dt, J=7.6, 1.6 Hz, 1H), 8.21 (t, J=1.8 Hz, 1H), 7.70 (t, J=7.8 Hz, 1H), 7.67 (dt, J=7.8, 1.6 Hz, 1H), 5.66 (s, 2H), 3.87-3.82 (m, 4H), 1.76-1.70 (m, 6H). $^{13}C$ NMR (151 MHz, $CDCl_3$) δ 164.1, 161.2, 160.2, 159.2, 152.9, 136.0, 132.2, 130.1, 129.1, 127.5, 124.5, 117.2, 115.9, 83.6, 81.6, 49.6, 26.2, 24.4. MS ($ESI^+$) calculated for $C_{20}H_{17}N_7O$: $[M+H^+]$ m/z=372.2, found m/z=372.4. HRMS ($ESI^+$) calculated for $C_{20}H_{17}N_7O$: $[M+H^+]$ m/z=372.1568, found m/z=372.1565.

Example 2: Effects of Compounds of the Invention in CHO Cells

The potency of the compounds of the invention was tested using adenosine receptor-expressing cells as described below.

a) Characterization of Potency Using Adenosine Receptor-Expressing Cells

Chinese Hamster Ovary (CHO) cells containing an in-house cAMP-based biosensor, described below, and expressing recombinant A2AR were used to characterize the potency of A2AR antagonists according to the invention. The biosensor contains a cAMP binding domain allowing the measurement of Gs and Gi-coupled receptors activation. Cells were treated in a 384 well plate with the indicated concentrations of A2AR antagonists, followed by the addition of an A2AR agonist, adenosine. cAMP levels were measured on a luminescent/fluorescent plate reader.

CHO cells expressing A2AR and the biosensor were seeded in a black 384-well plate (Nunc) and grown at 37° C. and 5% $CO_2$ overnight. They were pre-incubated for 6 minutes with compounds of the present invention at varied concentrations up to 30 μM, before adding the corresponding $EC_{80}$ of A2AR agonist, 400 nM of adenosine (Sigma). The cAMP biosensor allowed real-time monitoring of signals using an FDSS/μCELL (Hamamatsu). The assay was conducted in 1× Hanks Balanced Salt Solution (HBSS). The total volume of the reaction was 80 μl (45 μl of cells, 15 μl of antagonist and 20 μl of agonist). Data analysis was performed using GraphPad Prism.

Compounds of the invention were capable of antagonizing the production of cAMP in cell lines that overexpress A2AR, in the absence of other adenosine receptors, as reported in Table 1 below where the activity represents the ability of the compound to antagonize the production of cAMP in response to stimulation of A2AR-expressing CHO cells with the A2AR agonist adenosine, as described in the above cAMP assay methods. Therefore, the compounds can be classified as A2AR antagonists.

TABLE 1

| Compound | Activity |
|---|---|
| 3 | +++ |
| 4 | +++ |
| 5 | +++ |
| 6 | + |
| 9 | + |
| 7 | ++ |
| 8 | ++ |
| 12 | ++ |
| 11 | +++ |
| 14 | +++ |
| 10 | +++ |
| 13 | +++ |
| 15 | ++ |
| 16 | + |
| 18 | ++ |
| 21 | ++ |
| 22 | +++ |
| 24 | +++ |
| 25 | +++ |
| 26 | ++ |
| 27 | ++ |
| 28 | +++ |
| 29 | +++ |
| 30 | +++ |
| 31 | +++ |
| 32 | ++ |

The activity scale denotes an IC50 range of:
+: >1000 nM,
++: 200-1000 nM,
+++: <200 nM.

b) Verification of Negative Allosteric Molecular Mode of Action of Small Molecules Using 'Shift Assay'

'Shift assay' using an A2AR-transfected cell line is used to demonstrate the allosteric molecular mode of A2AR inhibition mediated by compounds of the present invention. Those assays use CHO cells containing a BRET-based biosensor and expressing recombinant A2AR, a 'shift assay' was performed in a 384-well plate, with the addition of the indicated concentrations of A2AR antagonists, followed by the addition of a concentration-response curve (CRC) of an A2AR agonist, adenosine. cAMP levels were measured on a luminescent/fluorescent plate reader. Briefly, CHO cells expressing A2AR and the biosensor were seeded in a black 384-well plate and grown at 37° C. and 5% $CO_2$ overnight. They were pre-incubated for 6 minutes with compounds of the present invention at various concentrations up to 30 μM, before adding adenosine at increasing concentrations up to 1 mM (CRC). The cAMP biosensor readings and assay volumes were as described in the previous section. Data analysis was performed using GraphPad Prism. A Schild regression plot was calculated for the compounds by using the shift assay data. The Log(DoseRatio-1) was plot on the y axis against the Log of the antagonist concentration on the x axis.

Negative allosteric modulation of A2AR can be identified using the 'shift assay'. The results are presented under FIG. 1A where it can be observed that the concentration-response curves (CRCs) of adenosine begin to overlap one another other as the compound concentration is increased (small open circles to larger open circles). Transformation of this data into a Schild regression plot (FIG. 1B), confirms this classification of compounds of the invention as NAMs because allosteric modulators cause a plateau of the dose-ratios (DR), observed at the top right of the Schild plot. In contrast, orthosteric compounds are characterized by a completely linear DR profile in a Schild regression plot (Kenakin, 2017, *Curr Protoc Pharmacol* doi: 10.1002 cpph.18).

Example 3: Effects of Compounds of the Invention on Immune Response Restoration in Healthy Human Peripheral Blood Immune Cells Human peripheral blood mononuclear cells (PBMCs) were isolated using density centrifugation from fresh whole blood of healthy human blood donors. Cells were cryopreserved and thawed and rested for several hours in complete cell culture media containing human albumin and antibiotics (penicillin and streptomycin; 100 units or mg per ml respectively). Cells were incubated in 96-well microplates with the indicated concentration of A2AR antagonists of the invention, followed by the addition of 5 UM of adenosine-5'-N-Ethyluronamide (NECA)—an adenosine analog that is a potent A2AR agonist doi.org/10.1371/journal.pcbi.1007818. DMSO was used as the storage diluent for concentrated A2AR antagonists. NECA and DMSO controls (% v/v) were also tested in parallel to the therapeutic candidates. After the indicated incubation time with NECA, cells were either stained to determine their intracellular level of pCREB, or activated with Dynabeads overnight before staining for intracellular cytokines, as described below.

a) Evaluation of Intracellular pCREB Using Flow Cytometry

The ability of compounds of the invention to restore normal pCREB levels in human-derived immune cells was tested as follows.

PBMCs that were cultured with A2AR antagonists in the presence of NECA and were subsequently fixed and permeabilized using ice cold paraformaldehyde and methanol-based kit reagents (ThermoFisher and Miltenyi, respectively). Cells were washed with FACS buffer and stained with fluorochrome-conjugated antibodies directed against the following antigens: pCREB (phosphorylated at serine 133), CD4, CD8—all sourced from Life Technologies, and CD3 (BD Biosciences). Stained cells were acquired using a Fortessa flow cytometer (BD). Gating of the desired cell subsets was performed using FSC-A vs FSC—H to remove doublet cells, FSC vs SSC parameters to identify cells with lymphocyte-like morphology, followed by $CD3^+$ T cell and $CD4^+$ or $CD8^+$ sub-gating. The fold change in mean fluorescence intensity (MFI) of intracellular pCREB in gated CD4 or $CD8^+$ T cells was calculated using NECA-only conditions, and divided by NECA and A2AR antagonist-cultured cells from the same donor. The overall activity of the tested compounds was calculated using the average of at least 3 donors.

Compounds of the invention were tested in physiological conditions using healthy human peripheral blood mononuclear cells as well as in the presence of human albumin to increase the physiological relevance of the assay. The compounds of the invention were also compared to control molecules which have been reported previously to antagonize A2AR (orthosteric antagonists) and have been tested in human Phase I or II clinical trials. These include CPI-444, 7-(5-methylfuran-2-yl)-3-[[6-[[(3S)-oxolan-3-yl]oxymethyl]pyridin-2-yl]methyl]triazolo[4,5-d]pyrimidin-5-amine (Ciforadenant), PBF-5091, 5-bromo-2,6-di(pyrazol-1-yl)pyrimidin-4-amine (Taminadenant), MK-38141, 4-(furan-2-yl)-10-[2-[4-[4-(2-methoxyethoxy)phenyl]piperazin-1-yl]ethyl]-3,5,6,8,10,11-hexazatricyclo[7.3.0.$0^{2,6}$]dodeca-1(9),2,4,7,11-pentaen-7-amine (Preladenant) AZD4635, 6-(2-chloro-6-methylpyridin-4-yl)-5-(4-fluorophenyl)-1,2,4-triazin-3-amine (Imaradenant), and AB928, 3-[2-Amino-6-[1-[[6-(2-hydroxypropan-2-yl)pyridin-2-yl]methyl]triazol-4-yl]pyrimidin-4-yl]-2-methylbenzonitrile (Etrumadenant), and two other known orthosteric compounds. Table 2 below represents the ability of the compounds to restore pCREB to normal physiological levels (immuno-competency) in gated human $CD4^+$ cells and Table 3 represents the ability of compounds to restore pCREB to normal physiological levels (immuno-competency) in gated human $CD8^+$ cells as described above. The activity scale represented is the average for at least 3 donors, compared to the NECA-only control.

TABLE 2

| Compound at 1 μM | Activity |
|---|---|
| none | – |
| 3 | ++++ |
| 4 | ++++ |
| 5 | ++++ |
| 11 | +++ |
| 13 | ++ |
| 24 | +++ |
| 28 | ++++ |
| 30 | ++ |
| 31 | ++ |
| Imaradenant | ++ |
| Ciforadenant | +++ |
| Preladenant | +++ |
| Etrumadenant | ++++ |
| Taminadenant | + |

TABLE 3

| Compound at 1 μM | Activity |
|---|---|
| none | – |
| 3 | ++++ |
| 4 | ++++ |
| 5 | ++++ |
| 11 | +++ |
| 13 | ++ |
| 24 | ++ |
| 28 | +++ |
| 30 | + |
| 31 | + |
| Imaradenant | ++ |
| Ciforadenant | +++ |
| Preladenant | +++ |
| Etrumadenant | ++++ |
| Taminadenant | + |

The activity scale denotes the restoration of a normal anti-tumor response which is assessed by the measure of pCREB level in CD4+ and CD8+ T cells. The minimum of the anti-tumor response is measured in immunocompromised conditions (NECA immunosuppression, without A2AR antagonist) and the normal response in immunocompetent conditions (without NECA and A2AR antagonists).

'–' denotes no reduction,

'+' denotes 0 to 40% reduction,

'++' denotes 40 to 70% reduction,

'+++' denotes 70 to 90% reduction, and

'++++' denotes over 90% reduction.

Reduction of pCREB corresponds to restoration of a normal anti-tumor immune response.

As it can be seen on Table 2 and 3, compounds of the invention were able to restore the normal physiological levels of pCREB in both CD4 and $CD8^+$ T cells in conditions mimicking high adenosine concentrations. pCREB is a signaling element which is proximal (downstream) to cAMP upon A2AR signaling, and represents a surrogate marker for immunosuppression.

b) Evaluation of Intracellular Cytokines Using Flow Cytometry

The ability of compounds of the invention to restore anti-tumor cytokine responses in human-derived immune cells was tested as described below.

Additionally, PBMCs that were cultured with A2AR antagonists and NECA were stimulated overnight with 1 μl of anti-CD3 and anti-CD28 Dynabeads (Life Technologies) in order to activate T cells, in the presence of GolgiStop (Life Technologies) to prevent secretion of any newly-induced cytokines. Cells were then stained with: a fixable live-dead stain (LD Blue, Life Technologies), the T cell-specific Abs described for the pCREB stain, followed by fixation and permeabilization with commercial kit containing paraformaldehyde and a detergent-based buffer (ThermoFisher). Intracellular staining for cytokines was performed using fluorochrome-conjugated antibodies directed against tumor necrosis factor alpha (TNF-α), interleukin 2 (IL-2), and interferon gamma (IFN-γ) diluted in permeabilization buffer (ThermoFisher). Cells were then washed, acquired, and gated as described for the pCREB assay with the following modifications: dead cells were excluded using the live-dead marker, and gated T cell subsets were then analyzed for the percentage of cytokine positive cells, which was a sub-gate of total $CD4^+$ or $CD8^+$ T cells. The percentage of cytokine positive cells in Dynabead-only control samples was used as the 100% normal (immuno-competent) immune response standard within each donor, whereas the Dynabead plus NECA stimulation condition represents an immunosuppressed control. Restoration of the cytokine response in the presence of A2AR antagonists was calculated as follows, using the average of at least 2 donors: 100×(1−(100−% cytokine positive cells in presence of A2AR antagonist)/(100−% cytokine positive cells in immuno-competent control)).

Compounds were tested in a translational assay involving activation of healthy donor human T cells in vitro, in the presence of an immunosuppressive concentration of the A2AR agonist NECA—as described above. The ability of compounds to restore normal cytokine production in activated human blood $CD4^+$ T cells and normal cytokine production in activated human blood $CD8^+$ T cells is represented in Tables 4 and 5, respectively. Clinical stage antagonist compounds are described in Table 2.

TABLE 4

| Compound at 1 μM | TNF-α[2] | IL-2[2] | IFN-γ[2] |
|---|---|---|---|
| none | − | − | − |
| 3 | +++ | + | + |
| 4 | +++ | +++ | ND |
| 5 | ++++ | +++ | ++ |
| 11 | ++ | ++ | ++ |
| 24 | ++ | +++ | + |
| 28 | +++ | ++ | ++ |
| 30 | ++ | +++ | +++ |
| 31 | ++++ | ++++ | ++++ |
| Imaradenant | + | + | + |
| Ciforadenant | + | ++ | + |
| Preladenant | ++ | − | ++ |
| Etrumadenant | +++ | +++ | + |
| Taminadenant | − | − | − |

TABLE 5

| Compound at 1 μM | TNF-α[2] | IL-2[2] | IFN-γ[2] |
|---|---|---|---|
| none | − | − | − |
| 3 | +++ | +++ | + |
| 4 | ++++ | − | +++ |
| 5 | ++ | ++ | + |
| 11 | +++ | +++ | + |
| 24 | ++ | + | +++ |
| 28 | ++ | +++ | + |
| 30 | + | ++++ | +++ |
| 31 | ++++ | ++ | ++++ |
| Imaradenant | − | − | ND |
| Ciforadenant | + | − | +++ |
| Preladenant | +++ | ++ | ND |
| Etrumadenant | +++ | ++ | + |
| Taminadenant | + | + | ND |

[2]activity denotes restoration of the immune response by considering the minimum response in immunocompromised conditions (NECO immunosuppression + T cell activation, without A2AR antagonist), and maximum normal (immunocompetent) response (T cell activation in the absence of NECA and A2AR antagonists).
ND; not determined.

Representative results demonstrate that the capacity of $CD4^+$ T cells (Table 4) and $CD8^+$ T cells (Table 5) to secrete pro-inflammatory (anti-tumor) cytokines (TNF-α, IL-2, IFN-7) is restored in the presence of some clinical stage antagonist molecules or negative allosteric modulators of A2AR.

Example 4: In Vivo Effects of Compounds of the Invention in Mouse Tumor Models To demonstrate in vivo therapeutic activity of the A2AR antagonists, murine ectopic MC38 or CT26 (colon carcinoma) tumor models were used. Mouse colon tumor cells, CT26 (FenicsBio) and MC38 (Creative-Biogene), expressing a bioluminescent luciferase construct (Firefly luciferase under the control of the CMV promoter) were verified to be mycoplasma free. Cells were cultivated as recommended by manufacturers and injected (0.2-1 million cells, as indicated, for example from between 250'000 to 500'000 tumor cells) via the subcutaneous route into immunocompetent mice (Balb/c for CT26, and C57BL/6 for MC38). Tumor growth was monitored until the establishment of well-defined medium size tumors. Subsequently, mice were randomized and treated either by direct intratumoral injections or via systemic administration. Seven to fourteen days later, mice were randomized into groups with average tumor sizes of 50 $mm^2$. Mice were treated at least once daily via the indicated route and dose of compound. For combination therapy trials, mice were additionally treated with existing approved immunotherapies (in vivo grade anti-PD-1 or anti-CTLA ICI mAbs, purchased from commercial suppliers) via the intraperitoneal route at the indicated dose and frequency. Mice were monitored daily for adverse events, and tumor burden was measured either by calipers or via injection of luciferin D followed by whole mouse imaging using an IVIS Spectrum (Perkin Elmer) instrument. Compounds of the invention of structure (Ib) mediated significant decrease of tumor growth when compared to vehicle control treatment performed under similar conditions.

The invention claimed is:

1. A method for preventing resistance to anti-cancer immunotherapy and/or treating a cancer in a subject suffering from a cancer or at risk of suffering from resistance to anti-cancer immunotherapy, said method comprising administering a compound of Formula (I) or a pharmaceutical formulation thereof to a subject in need thereof, wherein Formula (I) is:

(I)

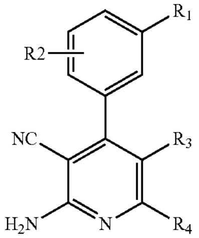

wherein $R_1$ is selected from a phenyl optionally substituted by one or more halogen, cyano, hydroxy or $C_1$-$C_6$ alkyl and five or six membered heteroaryl optionally substituted by one or more halogen, cyano, hydroxy or $C_1$-$C_6$ alkyl; $R_2$ is selected from H and halogen; $R_3$ is selected from H, CN and optionally substituted $C_1$-$C_6$ alkyl; $R_4$ is OR, where R is an optionally substituted $C_1$-$C_6$ alkyl or a $C_1$-$C_6$ hydroxyalkyl; SR, where R is an optionally substituted $C_1$-$C_6$ alkyl; XR(R'); an optionally substituted phenyl; or an optionally substituted five or six membered heteroaryl, wherein X is selected from O, S, N and R and R' are independently an optionally substituted $C_1$-$C_6$ alkyl, or XRR' form together an optionally substituted four to six membered heterocyclic alkyl, wherein the term "substituted" refers to groups substituted with from 1 to 3 substituents selected from the group consisting of halogen, cyano, nitro, hydroxy, amino (—$NH_2$, —NH—, —N—), amide (—NHC(O)—), carbonyl (—C(O)—), alkoxycarbonyl (—C(O)O—), carboxylic acid, ether (—O—), thioether (—S—), sulfoxide (—S(O)—), sulfone (—S$(O)_2$—), and $C_1$-$C_6$ alkyl, wherein said cancer is a solid tumor cancer.

2. A method for eliciting or increasing an immune response to immunotherapy, said method comprising administering an effective amount of one or more compound of Formula (I) or a pharmaceutical formulation thereof in combination with one or more of treatment selected from adoptive cell therapy, Chimeric Antigen Receptor T cell (CAR-T) therapy, tumor infiltrating lymphocyte (TIL) therapy, anti-cancer vaccine therapy or immunomodulating therapy comprising administering immune checkpoint inhibitors, bispecific T cell engagers, or nanobodies that bind to a single or multiple drug targets, wherein Formula (I) is:

(I)

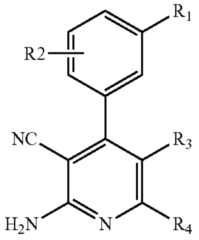

wherein $R_1$ is selected from a phenyl optionally substituted by one or more halogen, cyano, hydroxy or $C_1$-$C_6$ alkyl and a five or six membered heteroaryl optionally substituted by one or more halogen, cyano, hydroxy or $C_1$-$C_6$ alkyl; $R_2$ is selected from H and halogen; $R_3$ is selected from H, CN and optionally substituted $C_1$-$C_6$ alkyl; $R_4$ is OR, where R is an optionally substituted $C_1$-$C_6$ alkyl or a $C_1$-$C_6$ hydroxyalkyl; SR, where R is an optionally substituted $C_1$-$C_6$ alkyl; XR(R'); an optionally substituted phenyl; or an optionally substituted five or six membered heteroaryl, wherein X is selected from O, S, or N and R and R' are independently an optionally substituted $C_1$-$C_6$ alkyl, or XRR' form together an optionally substituted four to six membered heterocyclic alkyl.

3. The method according to claim 1, wherein $R_1$ is phenyl optionally substituted by one or more halogen, cyano, hydroxy or $C_1$-$C_6$ alkyl.

4. The method according to claim 1, wherein $R_1$ is selected from phenyl, halogeno phenyl or a $C_1$-$C_6$ alkyl phenyl.

5. The method according to claim 1, wherein $R_1$ is a five or six membered heteroaryl optionally substituted by one or more halogen, cyano, hydroxy or $C_1$-$C_6$ alkyl.

6. The method according to claim 1, wherein $R_1$ is an optionally substituted five or six membered heteroaryl selected from optionally substituted pyridinyl, optionally substituted thiophenyl, optionally substituted pyrazolyl and optionally substituted tetrazolyl, wherein optionally substituted refers to an optional substitution by one or more halogen, cyano, hydroxy or $C_1$-$C_6$ alkyl.

7. The method according to claim 1, wherein $R_2$ is H.

8. The method according to claim 1, wherein $R_3$ is CN.

9. The method according to claim 1, wherein $R_4$ is XR(R'), X is selected from O, S, or N and R and R' are independently an optionally substituted $C_1$-$C_6$ alkyl, or XRR' form together an optionally substituted four to six membered heterocyclic alkyl.

10. The method according to claim 1, wherein $R_4$ is a group OR wherein R is an optionally substituted $C_1$-$C_6$ alkyl.

11. The method according to claim 1, wherein $R_4$ is a group SR wherein R is an optionally substituted $C_1$-$C_6$ alkyl.

12. The method according to claim 1, wherein $R_4$ is selected from pyridine, pyrrolidine and azetidine.

13. The method according to claim 1, wherein $R_4$ is optionally substituted pyridine.

14. The method according to claim 1, wherein said compound is selected from the group consisting of:

4-([1,1'-biphenyl]-3-yl)-2-amino-6-(azetidin-1-yl)pyridine-3,5-dicarbonitrile;

4-([1, 1'-biphenyl]-3-yl)-2-amino-6-(pyrrolidin-1-yl)pyridine-3,5-dicarbonitrile;

4-([1, 1'-biphenyl]-3-yl)-2-amino-6-(piperidin-1-yl)pyridine-3,5-dicarbonitrile;

2-amino-4-(2'-fluoro-[1,1'-biphenyl]-3-yl)-6-(piperidin-1-yl)pyridine-3,5-dicarbonitrile;

2-amino-4-(3'-fluoro-[1,1'-biphenyl]-3-yl)-6-(piperidin-1-yl)pyridine-3,5-dicarbonitrile;

2-amino-4-(3'-fluoro-[1,1'-biphenyl]-3-yl)-6-(piperidin-1-yl)pyridine-3,5-dicarbonitrile;

2-amino-4-(2'-methyl-[1,1'-biphenyl]-3-yl)-6-(piperidin-1-yl)pyridine-3,5-dicarbonitrile;

2-amino-4-(3'-methyl-[1,1'-biphenyl]-3-yl)-6-(piperidin-1-yl)pyridine-3,5-dicarbonitrile;

2-amino-4-(4'-methyl-[1, 1'-biphenyl]-3-yl)-6-(piperidin-1-yl)pyridine-3,5-dicarbonitrile;

2-amino-6-(piperidin-1-yl)-4-(3-(pyridin-2-yl)phenyl)pyridine-3,5-dicarbonitrile;

2-amino-6-(piperidin-1-yl)-4-(3-(pyridin-3-yl)phenyl)pyridine-3,5-dicarbonitrile;

2-amino-6-(piperidin-1-yl)-4-(3-(pyridin-4-yl)phenyl)pyridine-3,5-dicarbonitrile;

2-amino-6-(piperidin-1-yl)-4-(3-(thiophen-2-yl)phenyl) pyridine-3,5-dicarbonitrile;
2-amino-6-(piperidin-1-yl)-4-(3-(thiophen-3-yl)phenyl) pyridine-3,5-dicarbonitrile;
4-(3-(1H-pyrazol-5-yl)phenyl)-2-amino-6-(piperidin-1-yl)pyridine-3,5-dicarbonitrile;
4-(3-(1H-tetrazol-5-yl)phenyl)-2-amino-6-(piperidin-1-yl)pyridine-3,5-dicarbonitrile;
4-([1, 1'-biphenyl]-3-yl)-2-amino-6-(diethylamino)pyridine-3, 5-dicarbonitrile;
4-([1, 1'-biphenyl]-3-yl)-2-amino-6-morpholinopyridine-3,5-dicarbonitrile;
4-([1, 1'-biphenyl]-3-yl)-2-amino-6-(bis(2-hydroxyethyl) amino) pyridine-3,5-dicarbonitrile;
4-([1, 1'-biphenyl]-3-yl)-2-amino-6-(4-methylpiperazin-1-yl)pyridine-3,5-dicarbonitrile;
4-([1,1'-biphenyl]-3-yl)-2-amino-6-((2-hydroxyethyl) amino) pyridine-3,5-dicarbonitrile;
4-([1, 1'-biphenyl]-3-yl)-2-amino-6-(diisopropylamino) pyridine-3,5-dicarbonitrile;
4-([1, 1'-biphenyl]-3-yl)-2-amino-6-(benzylamino)pyridine-3,5-dicarbonitrile;
4-([1,1'-biphenyl]-3-yl)-2-amino-6-(benzylthio)pyridine-3,5-dicarbonitrile;
4-([1, 1'-biphenyl]-3-yl)-2-amino-6-methoxypyridine-3, 5-dicarbonitrile;
4-([1,1'-biphenyl]-3-yl)-2-amino-6-ethoxypyridine-3,5-dicarbonitrile;
4-([1,1'-biphenyl]-3-yl)-2-amino-6-(2-hydroxyethoxy) pyridine-3,5-dicarbonitrile;
4-([1, 1'-biphenyl]-3-yl)-2-amino-6-(benzyloxy)pyridine-3,5-dicarbonitrile;
2-amino-4-(3-(3-fluoropyridin-2-yl)phenyl)-6-(piperidin-1-yl)pyridine-3,5-dicarbonitrile;
2-amino-4-(3-(6-fluoropyridin-2-yl)phenyl)-6-(piperidin-1-yl)pyridine-3,5-dicarbonitrile;
2-amino-4-(3-(4-fluoropyridin-2-yl)phenyl)-6-(piperidin-1-yl)pyridine-3,5-dicarbonitrile;
2-amino-4-(3-(5-fluoropyridin-3-yl)phenyl)-6-(piperidin-1-yl)pyridine-3,5-dicarbonitrile;
2-amino-4-(3-(2-fluoropyridin-3-yl)phenyl)-6-(piperidin-1-yl)pyridine-3,5-dicarbonitrile;
2-amino-4-(2-fluoro-5-(pyridin-3-yl)phenyl)-6-(piperidin-1-yl)pyridine-3,5-dicarbonitrile;
2-amino-4-(2-fluoro-3-(pyridin-3-yl)phenyl)-6-(piperidin-1-yl)pyridine-3,5-dicarbonitrile;
2-amino-4-(3-fluoro-5-(pyridin-3-yl)phenyl)-6-(piperidin-1-yl)pyridine-3,5-dicarbonitrile; and
4-(3-(1,3,4-oxadiazol-2-yl)phenyl)-2-amino-6-(piperidin-1-yl)pyridine-3,5-dicarbonitrile.

15. The method according to claim 1, wherein said compound is administered in combination with one or more of treatment selected from adoptive cell therapy, CAR-T therapy, TIL therapy, anti-cancer vaccine therapy, tumor specific antibodies, immunomodulating therapy, an anti-cancer immunotherapeutic agent, and immune checkpoint inhibitors.

16. The method according to claim 1, wherein said cancer is selected from lung cancer, breast cancer, ovarian cancer, cervical cancer, uterus cancer, head and neck cancer, melanoma, cancers of the digestive system, hepatocellular carcinoma, colon cancer, rectal cancer, colorectal carcinoma, kidney cancer, prostate cancer, gastric cancer, bronchus cancer, pancreatic cancer, urinary bladder cancer, hepatic cancer and brain cancer.

* * * * *